United States Patent
Layton et al.

(10) Patent No.: US 6,184,370 B1
(45) Date of Patent: *Feb. 6, 2001

(54) RECEPTOR-BINDING DETERMINANT FROM LEUKAEMIA INHIBITORY FACTOR

(75) Inventors: Meredith Jane Layton, Tecoma; Catherine Mary Owczarek, Carlton; Nicos Antony Nicola, Mont Albert; Nicholas Martin Gough, North Balwyn; Donald Metcalf, Balwyn, all of (AU)

(73) Assignee: Amrad Corporation Limited, Victoria (AU)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/505,187

(22) PCT Filed: Feb. 3, 1994

(86) PCT No.: PCT/AU94/00047

§ 371 Date: Sep. 27, 1995

§ 102(e) Date: Sep. 27, 1995

(87) PCT Pub. No.: WO94/18236

PCT Pub. Date: Aug. 18, 1994

(30) Foreign Application Priority Data

Feb. 3, 1994 (AU) .................................... PL 7102

(51) Int. Cl.$^7$ ............................ C07K 14/52; C12N 5/10; C12N 15/19; C12N 15/62
(52) U.S. Cl. ............... 536/23.4; 530/351; 435/69.5; 435/69.7; 435/71.1; 435/71.2; 435/471; 435/325; 435/252.3; 435/320.1; 536/23.5
(58) Field of Search ................................ 530/300, 350, 530/402, 351; 435/7.1, 69.1, 252.3, 69.5, 69.7, 71.1, 71.2, 471, 325, 254.11, 320.1; 536/23.5, 23.1, 23.4

(56) References Cited

FOREIGN PATENT DOCUMENTS

2500393 * 3/1993 (AU) .
0285448 * 10/1988 (EP) .

OTHER PUBLICATIONS

Godard et al. (1993) Cytokine 5:16–23.*
Kim et al. (1992) J. Immunol. Meth. 156: 9–17.*
Fukuda et al. (1992) Neuroreport 3:157–160.*
Ngo et al. In The Protein Folding Problem and Tertiary Structure Prediction (1994), Merz et al. (ed.) Birkhanser, Boston, MA, pp. 433, 452–495.*
Schultz et al. Principles of Protein Structure (1979), Springer, NY, NY, pp. 14–16.*
Owczarck et al. (1993) Embo J. 12:3487–3495.*
Moreau et al. (1988) 336:690–692 Nature.*
Willson et al. Eur. J. Bio Chem. 204(1), pp. 21–30, 1992.*
Ho et al. Gene 77(1) pp. 51–59, 1989.*
Schultz et al. Principles of Protein Structure, Springer, N.Y., pp. 14–16, 1979.*

* cited by examiner

*Primary Examiner*—Prema Mertz
(74) *Attorney, Agent, or Firm*—Scully, Scott, Murphy & Presser

(57) ABSTRACT

The present invention relates generally to molecules carrying one or more binding determinants for α-chain of human Leukaemia Inhibitory Factor binding receptor and to genetic sequences encoding same. More particularly, the present invention contemplates a molecule which is non-naturally occurring and which comprises a carrier portion and an active portion and wherein the active portion comprises amino acid residues or chemical equivalents thereof which constitute a binding determinant for the α chain of the human leukaemia inhibitory factor (hLIF) binding receptor.

22 Claims, 9 Drawing Sheets

Figure 1B:
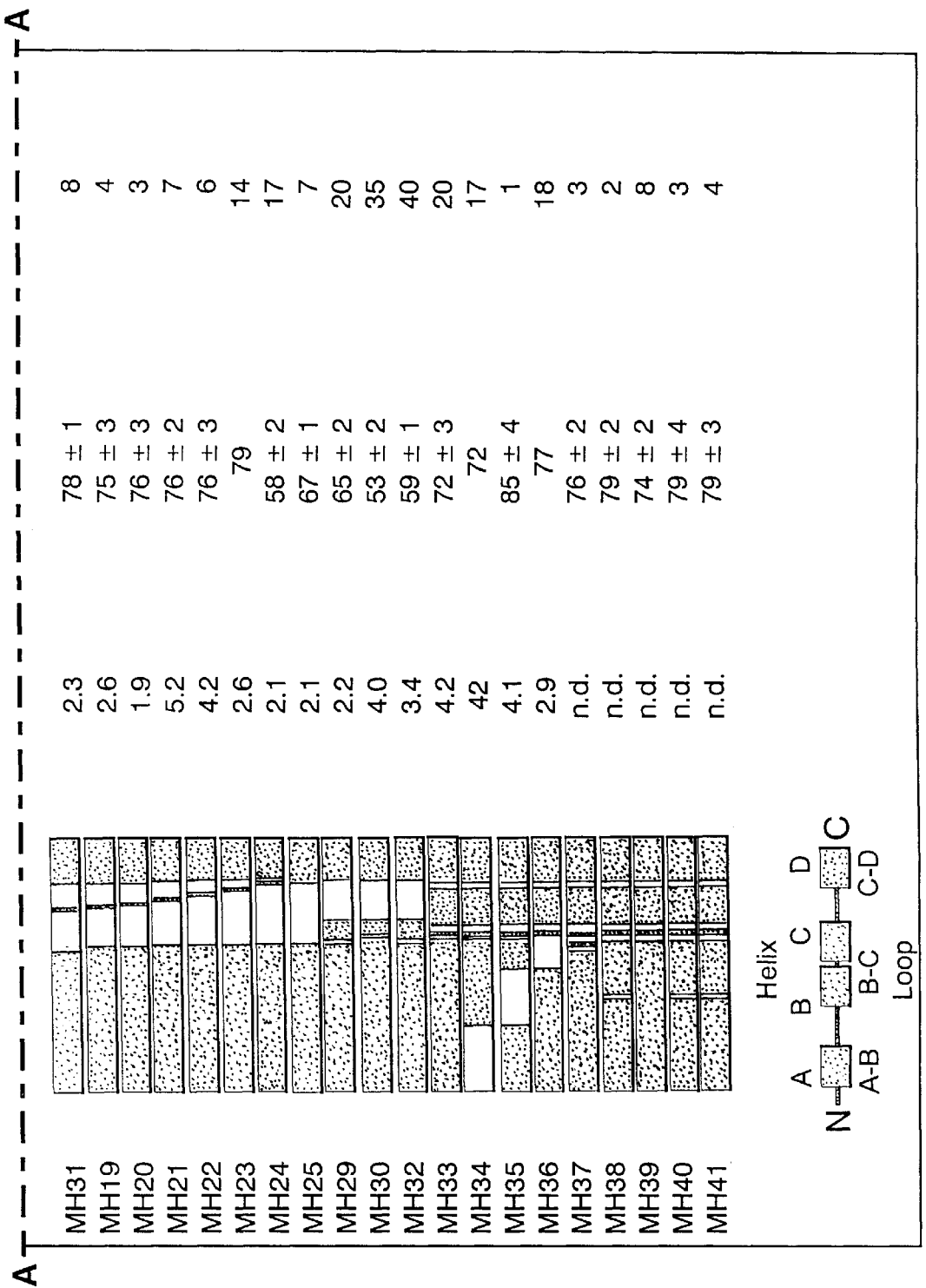

| HYBRID | SPECIFIC ACTIVITY (UNITS/mg) ×10⁻⁸ | SCORE (% HUMAN) MEAN ± S.E.M. (%) | ID$_{50}$(hybrid)/ID$_{50}$(hLIF) hLIF-R α-CHAIN |
|---|---|---|---|
| M | 2.2 | 0 | - |
| H | 3.8 | 100 | 1 |
| MH1 | 1.4 | 23 ± 3 | 30 |
| MH26 | 2.4 | 42 ± 3 | 150 |
| MH2 | 1.8 | 87 ± 4 | 3 |
| MH3 | 0.8 | 0 ± 0 | 1500 |
| MH4 | 2.4 | 26 ± 1 | 60 |
| MH5 | 1.6 | 52 ± 1 | 40 |
| MH6 | 1.4 | 78 ± 2 | 8 |
| MH15 | 1.1 | 92 | 3 |
| MH7 | 1.9 | 54 ± 4 | 20 |
| MH8 | 1.8 | 77 ± 3 | 6 |
| MH9 | 1.7 | 20 | 400 |
| MH10 | 1.5 | 80 ± 4 | 4 |
| MH11 | 1.4 | 67 ± 1 | 12 |
| MH12 | 1.5 | 73 ± 3 | 6 |
| MH13 | 1.4 | 73 ± 3 | 6 |
| MH27 | 2.0 | 66 ± 2 | 8 |
| MH28 | 4.4 | 60 ± 3 | 10 |
| MH14 | 2.9 | 71 ± 2 | 410 |
| MH16 | 1.7 | 60 ± 4 | 5 |
| MH17 | 3.8 | 68 ± 3 | 6 |
| MH18 | 1.3 | 79 ± 3 | 8 |

Figure 1(A)

```
           +1              10              20              30              40              50              60
MOUSE      GSPLPITPVNATCAIRHPCH GNLMNQIKNQLAQLNGSANALFISYYTA QGEPFPNNVEKLC
HUMAN      * * * * * * * * * * * * * * * * * *    * * N * * * RS * * * * * * * * * * L * * * *    * * * * LD * * *
PORCINE    * * * * S * * * * * * * * T * * * *    * * * KN * * * S * * * * * * * H * * S * *    * * * * LD * * *
G-CSF      ATPLGPASSL PQSFLLKCLEQVRKIQGDGAALQEKLCATYKLCHPEELVLLG
                      SShHHHHHHHHHHHHHHHHHHHHHHHHh    gGGGgGGhH
                         N-TERMINAL LOOP                A-HELIX                                      A-B LOOP 70              80              90             100             110             120
           APNMTDFPSFHGNGTEKTKLVE LYRMVAYLSASLTNITRDQKVL NPTAVS LQVKLNATID
           G * * V * * * * * * * * P * * A * * * * * I * V * * GT * * G * * * * * * I * * * S * L * * * HS * * A *
           G * * B * N * * P * * A * * AR * * * * * I I A * * GA * * G * * * * * RS * * * G * VN * * HS * * A *
           HSLGI     PWAPLSSCPSQALQ LAGCLSCLHSGLFLYQGLLQAL EGISPE LGPTLDTLQL
                    tTTt  SSSS     hHHHHHHHHHHHHHHHHHHHHHH TTtTTT hHHHHHHHH
                    A-B LOOP                B HELIX                B-C LOOP         C HELIX 130             140             150             160             170             180
           VMRGLLSNVLCRL CNKYRVGHVDVPPVPDHSDKEAFQR KKLGCQLLGTYKQVISVVVQAF
           IL * * * * * * * * * * * S * * H * * * * * * TYG * * T * G * DV * * K * * I * A * LA * *
           SM * * * * * * * * * * * N * * H * A * * * * AYG * * T * G * DV * * K * * V * S * LAR * *
           DVADFATTIWQQMEELGMAPALQPTQGAMPAFASAFQRRAGGVLVASHLQSFLEVSYRVL RHLAQP
           HHHHHHHHHHHHHHHHHHHHHHHHHHHhHHHHHHHHHHHHHHHHHHHHHHHHhTt
                      C-D LOOP                                           D HELIX
```

Figure 4

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 181 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Gly Ser Pro Leu Pro Ile Thr Pro Val Asn Ala Thr Cys Ala Ile Arg
  1               5                  10                  15

His Pro Cys His Gly Asn Leu Met Asn Gln Ile Lys Asn Gln Leu Ala
             20                  25                  30

Gln Leu Asn Gly Ser Ala Asn Ala Leu Phe Ile Ser Tyr Tyr Thr Ala
         35                  40                  45

Gln Gly Glu Pro Phe Pro Asn Asn Val Glu Lys Leu Cys Ala Pro Asn
 50                  55                  60

Met Thr Asp Phe Pro Ser Phe His Gly Asn Gly Thr Glu Lys Thr Lys
 65                  70                  75                  80

Leu Val Glu Leu Tyr Arg Met Val Ala Tyr Leu Ser Ala Ser Leu Thr
                 85                  90                  95

Asn Ile Thr Arg Asp Gln Lys Val Leu Asn Pro Thr Ala Val Ser Leu
            100                 105                 110

Gln Val Lys Leu Asn Ala Thr Ile Asp Val Met Arg Gly Leu Leu Ser
        115                 120                 125

Asn Val Leu Cys Arg Leu Cys Asn Lys Tyr Arg Val Gly His Val Asp
    130                 135                 140

Val Pro Pro Val Pro Asp His Ser Asp Lys Glu Ala Phe Gln Arg Lys
145                 150                 155                 160

Lys Leu Gly Cys Gln Leu Leu Gly Thr Tyr Lys Gln Val Ile Ser Val
                165                 170                 175

Val Val Gln Ala Phe
            180
```

(2) INFORMATION FOR SEQ ID NO:2:

(i) SEQUENCE CHARACTERISTICS:
    (A) LENGTH: 181 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:2:

Gly Ser Pro Leu Pro Ile Thr Pro Val Asn Ala Thr Cys Ala Ile Arg
1               5                   10                  15

His Pro Cys His Asn Asn Leu Met Asn Gln Ile Arg Ser Gln Leu Ala
            20                  25                  30

Gln Leu Asn Gly Ser Ala Asn Ala Leu Phe Ile Leu Tyr Tyr Thr Ala
            35                  40                  45

Gln Gly Glu Pro Phe Pro Asn Asn Leu Asp Lys Leu Cys Gly Pro Asn
    50                  55                  60

Val Thr Asp Phe Pro Pro Phe His Ala Asn Gly Thr Glu Lys Ala Lys
65                  70                  75                  80

Leu Val Glu Leu Tyr Arg Ile Val Val Tyr Leu Gly Thr Ser Leu Gly
                85                  90                  95

Asn Ile Thr Arg Asp Gln Lys Ile Leu Asn Pro Ser Ala Leu Ser Leu
                100                 105                 110

His Ser Lys Leu Asn Ala Thr Ala Asp Ile Leu Arg Gly Leu Leu Ser
            115                 120                 125

Asn Val Leu Cys Arg Leu Cys Ser Lys Tyr His Val Gly His Val Asp
    130                 135                 140

Val Thr Tyr Gly Pro Asp Thr Ser Gly Lys Asp Val Phe Gln Lys Lys
145                 150                 155                 160

Lys Leu Gly Cys Gln Leu Leu Gly Lys Tyr Lys Gln Ile Ile Ala Val
                165                 170                 175

Leu Ala Gln Ala Phe
            180

(2) INFORMATION FOR SEQ ID NO:3:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Gly Ser Pro Leu Ser Ile Thr Pro Val Asn Ala Thr Cys Ala Thr Arg
1               5                   10                  15

His Pro Cys His Ser Asn Leu Met Asn Gln Ile Lys Asn Gln Leu Ala
            20                  25                  30

His Leu Asn Ser Ser Ala Asn Ala Leu Phe Ile Leu Tyr Tyr Thr Ala
            35                  40                  45

Gln Gly Glu Pro Phe Pro Asn Asn Leu Asp Lys Leu Cys Gly Pro Asn
    50                  55                  60

Xaa Thr Asn Phe Pro Pro Phe His Ala Asn Gly Thr Glu Lys Ala Arg
65                  70                  75                  80

Leu Val Glu Leu Tyr Arg Ile Ile Ala Tyr Leu Gly Ala Ser Leu Gly
                85                  90                  95

Asn Ile Thr Arg Asp Gln Arg Ser Leu Asn Pro Gly Ala Val Asn Leu
                100                 105                 110

```
His Ser Lys Leu Asn Ala Thr Ala Asp Ser Met Arg Gly Leu Leu Ser
        115                 120                 125

Asn Val Leu Cys Arg Leu Cys Asn Lys Tyr His Val Ala His Val Asp
        130                 135                 140

Val Ala Tyr Gly Pro Asp Thr Ser Gly Lys Asp Val Phe Gln Lys Lys
145                 150                 155                 160

Lys Leu Gly Cys Gln Leu Leu Gly Lys Tyr Lys Gln Val Ile Ser Val
                165                 170                 175

Leu Ala Arg Ala Phe
            180

(2) INFORMATION FOR SEQ ID NO:4:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Ala Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

RECEPTOR-BINDING DETERMINANT FROM LEUKAEMIA INHIBITORY FACTOR

The present invention relates generally to molecules carrying one or more binding determinants for the α-chain of human Leukaemia Inhibitory Factor binding receptor and to genetic sequences encoding same.

Bibliographic details of the publications referred to in this specification are collected at the end of the description. Sequence Identity Numbers (SEQ ID NOs.) for amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Certain aspects of the present invention relate to leukaemia inhibitory factor (hereinafter referred to as "LIF") of human (h) (SEQ. ID. No:2) or murine (m) (SEQ. ID. NO:1) origin or to combinations thereof. Where reference is made to amino acid residues in these molecules, the residues are numbered consecutively from the first serine residue of the mature, native protein (see FIG. 4). In certain circumstances, the production of recombinant LIF molecules may involve a fusion protein with glutathione-S-transferase (GST) in an expression vector system. Agents such as thrombin may be used to cleave the GST portion of the LIF-GST molecule which can result in an additional glycine residue at position −1 (FIG. 4). Murine and human LIF hybrids (MH) referred to in the specification are defined in Table 1 and FIG. 1. The legend to Table 1 describes the nomenclature used to define the hybrid structures. It should be noted that the numbering system of amino acid residues referred to in Australian Provisional Application No. PL7102 filed on Feb. 3, 1993 and from which the present application claims priority starts at the initiating methione of the immature, native protein. Accordingly, the serine at position +1 described in the present specification corresponds to position +24 in the aforementioned provisional application.

LIF is a glycoprotein that was originally purified and cloned on the basis of its ability to induce terminal macrophage differentiation of the M1 myeloid leukaemic cell line (Hilton et al. 1988a). It has since been shown to have a variety of activities on a wide range of cell types including megakaryocytes, osteoblasts, hepatocytes, adipocytes, neurons, embryonal stem cells and primordial germ cells (Metcalf, 1991).

It is proposed that LIF transduces its biological signal via a multi-subunit membrane-bound receptor. The receptor for LIF is a member of the haemopoietin or cytokine family of receptors, which generally have roles in cell growth and differentiation. These receptors are characterised by their extracellular domain, which contains at least one copy of an approximately 200 amino acid haemopoietin domain (Cosman, 1990). A number of primary amino acid sequence motifs distinguish this domain, including pairs of disulfide-bonded cysteine residues and the Trp-Ser-X-Trp-Ser motif (where X is any amino acid). The overall secondary and tertiary fold of the haemopoietin domain is predicted to be similar in each member of the receptor family (Bazan, 1990a). Like the extracellular domain of the growth hormone receptor (de Vos et al, 1992), the 200 amino acids of the haemopoietin domain form 14 anti-parallel β-strands, folded into two barrel structures. The LIF receptor consists of two known subunits, both of which are members of the haemopoietin receptor family. The LIF receptor α-chain binds LIF with low-affinity and contains two haemopoietin domains (Gearing et al, 1991). The β-chain of the LIF receptor has been identified as gp130 (Gearing et al, 1992) which is also a component of the interleukin (IL)-6, IL-11, oncostatin M (OSM) and ciliary neurotrophic factor receptor (CNTF) complexes.

The ligands for this family of receptors are unrelated at the primary amino acid sequence level, but secondary and tertiary structural predictions indicate that all known ligands for haemopoietin receptors have a similar overall fold, suggesting evolution from a common ancestor (Bazan, 1990b). Members of this family of ligands form an anti-parallel, four α-helical bundle (the helices are designated A, B, C and D ordered from the N-terminus), that is characterised by one short and two long connecting loops (labelled by the helices they join). This has been shown for several ligands that are members of this family, including granulocyte colony-stimulating factor (G-CSF) (SEQ. ID. NO:4) (Hill et al, 1993), granulocyte-macrophage CSF (GM-CSF) (Diederichs et al, 1991), growth hormone (GH) (de Vos et al, 1992; Abdel-Meguid et al, 1987), IL-2 (Brandhuber et al, 1987), IL-4 (Powers et al, 1992) and IL-5 (Milburn et al, 1993), whose structures have been solved, either by x-ray crystallography or by NMR studies. The three-dimensional structure of LIF is predicted to be most similar to the structures of OSM, CNTF, IL-6 and G-CSF, amongst others.

Whilst murine LIF (mLIF) is unable to bind to the human LIF (hLIF) receptor (hLIF-R), hLIF (SEQ. ID. NO:2) is able to bind to both high- and low-affinity mouse LIF receptors (mLIF-R SEQ. ID. NO:1), and is fully biologically active on mouse cells. Intriguingly, hLIF (SEQ. ID. NO:2) binds to both the naturally occurring soluble form of the mLIF-R α-chain, mLIF-binding protein (mLBP) (Layton et al, 1992), and the high-affinity mLIF-R on PC.13 cells with a higher affinity than mLIF, due to markedly different dissociation kinetics. Competitive displacement curves showed that unlabelled mLIF (SEQ. ID. NO:1) and hLIF (SEQ. ID. NO:2) had a similar ability to complete with [$^{125}$I]mLIF, for binding to mLBP, while unlabelled hLIF was consistently 1000- to 5000-fold more effective than mLIF (SEQ. ID. NO:1) in competing with [$^{125}$I]hLIF for binding to mLBP (Layton et al, 1992). Mouse LBP is also able to act as a competitive inhibitor of LIF binding to its cellular receptor, leading to inhibition of biological responses to LIF. Again, mLBP was an approximately 1000-fold more potent inhibitor of hLIF (SEQ. ID. NO:2) than mLIF (SEQ. ID. NO:1) in this system. Thus, at least two features of hLIF (SEQ. ID. NO:2) distinguish it from mLIF (SEQ. ID. NO:1): first, its capacity to bind to the hLIF-R where mLIF (SEQ. ID. NO:1) cannot and second, its capacity to bind to the mLIF-R with higher affinity than does mLIF (SEQ. ID. NO:1).

Understanding the way in which a cytokine interacts with its receptor at a molecular level is required for the rational design of agonists and antagonists to growth factor and cytokine action as well as the design of growth factor and cytokine analogues. In work leading up to the present invention, the inventors exploited the differences in binding characteristics of murine (SEQ. ID. NO:1) and human LIF (SEQ. ID. NO:2) to identify a major determinant responsible for the binding of human LIF (hLIF) to the α-chain of its receptor. The present invention provides, for the first time, a rational approach to the generation of a new range of therapeutics based on LIF by providing non-naturally occurring molecules capable of binding to hLIF receptor. Such therapeutics may be both proteinaceous and non-proteinaceous molecules.

Accordingly, one aspect of the present invention contemplates a non-naturally occurring molecule comprising a tertiary structure which presents a functional binding face for the α-chain of hLIF binding receptor.

More particularly, the present invention is directed to a molecule which is non-naturally occurring and which comprises a carrier portion and an active portion wherein the tertiary structure of said active portion comprises non-contiguous amino acid residues or chemical equivalents thereof selected to constitute a binding determinant for the α-chain of human leukaemia inhibitory factor (hLIF) binding receptor.

This aspect of the present invention is predicated in part on the identification of the amino acid residues on hLIF (SEQ. ID. NO:2) which constitute the binding face for the hLIF receptor and in particular the α-chain of the hLIF receptor. Since a major contribution to the binding face is the three dimensional arrangement of chemically interactive groups on the side chains of the amino acid residues, a preferred aspect of the present invention relates to the non-naturally occurring molecule wherein the functional binding face comprises the chemically interactive groups of the amino acid residues which constitute the binding determinant on hLIF for the α-chain of hLIF binding receptor. The most preferred chemically interactive groups including groups selected from at least one of a methyl group, a hydroxyl group, an imino-nitrogen group, a negatively charged carboxyl group and a positively charged nitrogen group or chemical equivalents homologues or analogues thereof. These chemical groups are in spatial arrangement such that they present a binding face for the α-chain of the LIF binding receptor. In a most preferred embodiment, the chemical groups are presented on the amino acid residues themselves, or their chemical homologues, analogues or equivalents, which amino acid residues are selected from Gln 21 to Lys 160 of hLIF (SEQ. ID. NO:2). The amino acid residues are more particularly selected from at least one of each of the following regions of hLIF (SEQ. ID. NO:2):

(i) a region between A and B helices;

(ii) a region between the B and C helices;

(iii) the C helix; and (iv) a region between the C and D helices.

Even more particularly, amino acids are Asp 57, Ser 107, His 112, Ser 113, Val 155 and Lys 158 of hLIF (SEQ. ID. NO:2) or chemical homologues, analogues or equivalents thereof. In this embodiment of the present invention, the critical aspect of these amino acids is the chemically interactive group(s) on the side chains of each residue which, in defined spatial arrangement, constitute the binding face of hLIF for the α-chain of the hLIF binding receptor. It is clear, therefore, that the binding face does not need to comprise amino acid residues but the chemical interactive groups thereon.

The non-naturally occurring molecule may be any convenient carrier as described below including a solid support or matrix, or a non-proteinaceous molecule, or a protein, polypeptide or peptide. In a most preferred embodiment, the non-naturally occurring molecule in the form of a carrier is a mammalian cytokine such as but not limited to mLIF (SEQ. ID. NO:1) carrying the hLIF (SEQ. ID. NO:2) receptor-binding face.

The non-naturally occurring molecule may not necessarily carry the exact hLIF receptor-binding face of hLIF but will contain an amount of the hLIF receptor-binding face of hLIF to enable the non-naturally occurring molecule to exhibit at least about 35% and more preferably at least about 50% hLIF-like activity as described below.

According to a more preferred embodiment, there is provided a non-naturally occurring chemical entity such as a proteinaceous or non-proteinaceous molecule and/or a solid or non-immobilised support, said chemical entity comprising a tertiary structure which presents one or more chemically interactive groups selected from at least one of each of a methyl group, a hydroxyl group, an imino-nitrogen group, a negatively charged carboxyl group and a positively charged nitrogen group as a functional binding face for the α-chain of hLIF binding receptor. In a preferred embodiment, the non-naturally occurring chemical entity exhibits at least about 50% hLIF-like activity determined as described below.

Preferably, the chemically interactive groups are presented on amino acid residues selected from one or more of Asp, Ser, His, Val and Lys or their chemical equivalents, homologues or analogues. More preferably, the chemically interactive groups correspond to those on Asp 57, Ser 107, His 112, Ser 113, Val 155 and Lys 158 of hLIF (SEQ. ID. NO:2) or chemical homologues, analogues or equivalents thereof.

Another aspect of the present invention is directed to a molecule which is non-naturally occurring and which comprises a carrier portion and an active portion wherein said active portion comprises amino acid residues or chemical equivalents thereof which constitute a binding determinant for the α-chain of the hLIF binding receptor.

The term "molecule" is used in its broadest sense to refer to any chemical entity or compound, or a protein, polypeptide, or peptide or a non-peptide analogue and which is capable of carrying a sufficient number of amino acid residues or their chemical equivalents to constitute an effective binding determinant for the α-chain of the hLIF binding receptor. A "sufficient number" of amino acid residues is the minimum number required to exhibit at least 35% hLIF-like activity in terms of the ability to compete for $^{125}$I-hLIF binding to murine LIF-binding protein (mLBP) which is determined as described below. A "chemical equivalent" includes active and interactive groups present on a particular amino acid residue and, hence, extends to non-peptide or non-amino acid mimics of the amino acid residues involved in the binding face.

The "molecule" is considered a "carrier" of the amino acid residues or their analogues which constitute all or a functional part of a binding determinant for the α-chain of the hLIF binding receptor. The selection of an appropriate carrier molecule is determined by its tertiary structure. The amino acid residues or their analogues are required to form a receptor binding face in the tertiary structure of the carrier molecule. The present invention provides, therefore, a carrier molecule having a tertiary structure such that a sufficient number of amino acid residues or their analogues including chemical equivalents, constituting a binding determinant for the α-chain of the hLIF binding receptor, when introduced into said carrier molecule to form a receptor-binding face capable of at least 35% hLIF-like activity.

Preferably, the carrier molecule is a protein, polypeptide or peptide or a molecule substantially consisting of amino acid residues linked via peptide bonds. The molecules may also be engineered to contain non-naturally occurring amino acid residues such as some D-amino acids, non-naturally occurring substituted amino acids or chemical equivalents of amino acids which direct or otherwise influence the tertiary structure of the molecule. For example, a carrier molecule such as a protein, polypeptide or protein may be engineered to contain an amino acid, chemical derivative thereof or other chemical entity exhibiting conformational restraints on the overall molecule or a part thereof. Molecules exhibiting pre-determined tertiary conformations are particularly useful in their selection as carrier molecules in accordance with the present invention.

In a preferred embodiment, the carrier molecule is a mammalian cytokine such as but not limited to a non-human LIF, a colony stimulating factor (CSF) (e.g. G-CSF, GM-CSF) growth hormone, an interleukin (e.g. IL-2, IL-4, IL-6), oncostatin M (OSM), ciliary neurotrophic factor (CNTF) or other factor (e.g. a haemopoietic growth factor, interferon). Preferred non-human LIF molecules are those from livestock animals (e.g. from sheep, cattle, donkeys, horses, deer, goats and pigs), laboratory test animals (e.g. mice, rats and guinea pigs), companion animals (e.g. dogs and cats) or captive wild animals (e.g. kangaroos, foxes, dingos, wild boar and emus). The preferred non-human LIF is murine LIF (SEQ. ID. NO:1). The preferred cytokine is G-CSF (SEQ. ID. NO:4).

It is not a requirement of the present invention nor is the invention so limited that every amino acid residue forming the receptor binding face for the α-chain of hLIF-binding receptor on hLIF be existent on the carrier molecule. It is a requirement, however, that a sufficient number of the residues be present in sufficient conformational proximity such that the receptor-binding face is formed exhibiting at least about 35% hLIF-like activity. Furthermore, the amino acids present in hLIF forming the receptor-binding determinant may be substituted by one or more functionally equivalent amino acids or chemical derivatives thereof such that receptor binding activity is not completely lost. Accordingly, the present invention extends to a carrier molecule carrying amino acid residues or their chemical equivalents or derivatives or amino acid equivalents, homologues or analogues of the amino acids in hLIF which constitute the binding determinant for the α-chain of the hLIF binding receptor, wherein the number of amino acid residues and their proximity are sufficient for the molecule to exhibit at least about 35% hLIF-like activity and more preferably at least about 50% hLIF-like activity.

The amino acid residues constituting the binding determinant are selected from Gln 48 to Lys 160 of hLIF (SEQ. ID. NO:2) using the numbering system depicted in FIG. 4. Preferably, at least one amino acid residue is selected from each of the following regions of hLIF:

(i) a region between the A and B helices;

(ii) a region between the B and C helices;

(iii) the C helix; and (iv) a region between the C and D helices.

Even more preferably, the amino acid residues are selected from one or more of a Asp, Ser, His, Val and/or Lys or chemical equivalents thereof including chemically interactive groups thereon. The actual binding determinant on LIF comprises Asp 57, Ser 107, His 112, Ser 113, Val 155 and Lys 158 which, in a most preferred embodiment, forms the same arrangement or a functional equivalent arranged in the non-naturally occurring molecule. These amino acids are arranged in the carrier molecule such that at least two and more preferably at least three and even more preferably at least four residues are non-contiguous relative to each other.

Reference is made herein to the subject molecule having at least about 35% hLIF-like activity. More preferably, the molecule has at least about 50% hLIF-like activity and even more preferably at least about 70% hLIF-like activity. hLIF-like activity is defined in terms of the ability for a molecule to compete for $^{125}$I-hLIF binding to mLBP based on the equation:

$$\frac{\log x_m - \log x_c}{\log x_m - \log x_h} \times 100 = \% \text{ hLIF-like activity}$$

wherein $x_m$ is the dose of unlabelled mLIF; $x_h$ is the dose of unlabelled hLIF; $x_c$ is the dose of the molecule (e.g. protein, polypeptide or peptide) required to give 50% inhibition of $^{125}$I-hLIF binding to mLBP.

Accordingly, a preferred embodiment of the present invention contemplates a hybrid molecule comprising:

(i) a polypeptide backbone having a tertiary structure;

(ii) amino acid residues constituting a binding determinant for the α chain of hLIF binding receptor inserted into said polypeptide backbone such that the arrangement of said amino acid residues in the tertiary structure of the polypeptide provides a hLIF receptor binding face; and wherein said hybrid molecule exhibits at least about 50% hLIF-like activity as defined by the equation:

$$\frac{\log x_m - \log x_c}{\log x_m - \log x_h} \geq 0.50$$

wherein $x_m$ is a dose of unlabelled mLIF; $x_h$ is a dose of unlabelled hLIF; and $x_c$ is a dose of hybrid molecule required to give 50% inhibition of $^{125}$I-hLIF binding to murine LIF binding protein (mLBP).

With respect to this embodiment, the molecule is a hybrid between a carrier molecule in the form of a polypeptide and the amino acid residues forming the binding determinant for the α-chain of the hLIF-binding receptor. Preferably, the polypeptide is a mammalian cytokine as hereinbefore described. Preferably, the amino acid residues are selected from hLIF (SEQ. ID. NO:2) as hereinbefore described. This definition is also applicable when the carrier molecule and/or the binding interface are non-proteinaceous in a form such as a chemical compound capable of mimicking a polypeptide or peptide.

This embodiment of the present invention is conveniently elucidated by the following diagram which shows the competitive inhibition of mLIF (SEQ. ID. NO:1), hLIF (SEQ. ID. NO:2) and a hybrid LIF peptide or polypeptide with iodinated hLIF for the mLIF receptor:

A "peptide" is taken herein to be a molecule comprising ten or less amino acid residues. A "polypeptide" is a molecule comprising eleven or more amino acid residues and includes a protein. The peptides and polypeptides are preferably recombinant or synthetic molecules but extend to fragments or parts of naturally occurring LIF molecules and to hybrid molecules comprising regions from two or more LIF molecules from different species. Preferably, the peptides and polypeptides are "isolated" meaning that they have undergone at least one step toward biological purity. A peptide or polypeptide is deemed herein to be "isolated" or "biologically pure" where a preparation comprises at least 35%, preferably at least 45%, more preferably at least 55–60%, still more preferably at least 65–75% and even more preferably at least 80–90% of the peptide or polypeptide relative to other components in the preparation as determined by weight, LIF receptor-binding activity, amino acid content or other convenient means.

The present invention is particularly exemplified using a soluble murine LIF-binding protein (mLBP) (Layton et al, 1992) or a recombinant human LIF receptor which are convenient since human LIF readily binds or otherwise associates with these molecules. It is not intended, however, for the present invention to be limited solely to the murine receptor or to the elucidation of the binding determinant solely on the human LIF molecule.

As stated above, the molecules of the present invention are useful inter alia in rendering a LIF molecule from one species more like a LIF molecule from another species. The hybrid LIF molecule is also useful in designing drug analogues, agonists and antagonists.

Preferably, the hybrid LIF molecule is between non-human LIF and human LIF and most preferably between murine LIF (SEQ. ID. NO:1) and human LIF (SEQ. ID. NO:2). In accordance with these preferred embodiments, the hybrid LIF molecule is said to be a "humanised" form of non-human LIF and, in such a case, the humanised non-human LIF molecule may be more efficacious in humans and/or may provoke no or a reduced immune response compared to the non-human LIF molecule per se.

The present invention is particularly useful in designing analogues, antagonists and agonists based on the chemically interactive groups which constitute the binding face on hLIF (SEQ. ID. NO:2) for hLIF receptor. This permits a rational design of such molecules which can be readily assayed in vitro and in vivo. The present invention extends to all such analogues, antagonists and/or agonists capable of binding or otherwise interacting with the hLIF receptor binding face on a non-naturally occurring molecule, chemical entity or hybrid molecule as hereinbefore described.

Another embodiment of the present invention is directed to genetic sequences comprising a sequence of nucleotides which encode or are complementary to nucleotide sequences which encode the peptides and polypeptides encompassed by the present invention. The genetic sequences may be cDNA or mRNA and may be single or double stranded, linear or covalently closed, circular molecules. Conveniently, the genetic molecules are part of an expression vector capable of expression in a prokaryotic cell (e.g. *E. coli*) or a eukaryotic cell (e.g. an animal or mammalian cell).

The present invention further contemplates a method for mapping LIF receptor-binding activity associated with a mammalian LIF to one or more amino acid residues or to a sequence of amino acid residues on said LIF, said method comprising substituting for regions on said mammalian LIF, structurally similar regions from a LIF from a different species of mammal wherein both LIF molecules before substitution differ in respect of the activity to be mapped, assaying the substituted LIF molecules so obtained and identifying regions on one or both of said LIF molecules responsible for LIF receptor-binding activity.

Preferably, the substitutions are based on secondary structural predictions (see generally Bazan, 1991) such that the hybrids so constructed differ in the activity to be mapped. Preferably also, the substitution of regions are at the DNA level which are then expressed to form recombinant hybrid LIF molecules.

This aspect of the present invention is exemplified and described hereinafter by determining the LIF receptor-binding determinant on human LIF using a series of mouse-human LIF hybrid molecules some of which retain hLIF-like activity as previously described. The present invention, however, extends to the use of LIF molecules from other mammalian species.

The preferred hybrids comprise a murine LIF carrier molecule and a sufficient or effective number of amino acid residues from hLIF to constitute a receptor binding face for the α-chain of hLIF-binding receptor. Even more preferred amino acid residues or peptides are those which carry the hLIF binding determinant in MH5, MH6, MH16, MH17, MH18, MH31, MH19, MH20, MH21, MH22, MH23, MH24, MH25, MH29, MH30, MH32, MH33, MH34, MH35, MH36, MH37, MH38, MH39, MH40 and MH41. Still more preferred amino acids or peptides are those in MH33, MH35, MH36, MH37, MH38, MH40 and MH41. The most preferred amino acids or peptides are those in MH33, i.e. Ser 107, His 112, Ser 113, Val 155 and Lys 158 together with an amino acid selected from the region between the A and B helices, i.e. Asp 57.

The following single and three letter abbreviations for amino acid residues are used in the specification:

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The following other abbreviations are used in the specification:

| LIF | Leukaemia Inhibitory Factor |
|---|---|
| LIF-R | LIF receptor |
| m | murine |
| h | human |
| p | porcine |
| LBP | LIF binding protein |

IN THE FIGURES

FIG. 1 is a summary of data from biological assays and competitive binding assays of mLIF (SEQ. ID. NO:1), hLIF (SEQ. ID. NO:2) and chimeric LIF proteins. Mouse LIF (SEQ. ID. NO:1) sequence is represented by blue boxes and hLIF (SEQ. ID. NO:2) sequence is represented by yellow boxes. The hybrid proteins are numbered from 1 to 41 and are prefixed by "MH" to denote that they contain both mLIF and hLIF amino acid sequence. The relative positions of the predicted α-helices and connecting loops in the hybrid proteins can be determined by visual alignment of the schematic representations with the diagram immediately below. The percentage human score of mLIF, hLIF and hybrid proteins is calculated from the ID$_{50}$ for inhibition of [$^{125}$I]hLIF binding to mLIF-binding protein. Most assays were performed two or more times with essentially identical results. N.D., not determined. The exact amino acid construction of each hybrid according to SEQ ID NO. 2 is indicated in Table 1.

Figure 2A:
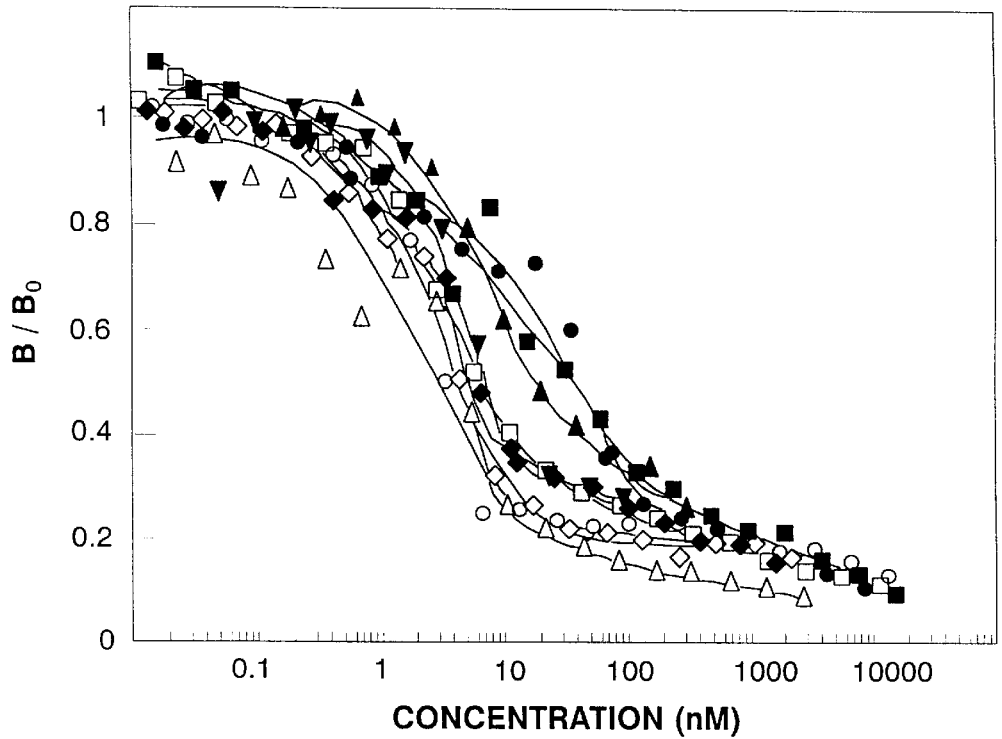

FIG. 2(A) Competitive inhibition of [$^{125}$I]mLIF binding to mLBP (soluble mLIF-R α-chain) by mLIF, hLIF and a selection of m-hLIF hybrids, (●) mLIF; (○) hLIF; (▲) MH1; (△) MH2; (■) MH3; (□) MH4; (◆) MH5; (◇) MH6; (▼) MH14. Results for all competition assays were expressed as the number of counts bound to the receptor at a particular concentration of unlabelled competitor (B) divided by the number of counts bound to the receptor when no unlabelled competitor was present (B$_0$). (B) Competitive inhibition of [$^{125}$I]hLIF binding to mLBP by mLIF, hLIF and a selection of m-hLIF hybrids. (●) mLIF; (○) hLIF; (▲) MH1; (△) MH2. (C) Competitive inhibition of [$^{125}$I]hLIF biding to mLBP by mLIF, hLIF and a selection of m-HLIF hybrids, (●) mLIF; (○) hLIF; (■) MH3; (□) MH4; (◆) MH5; (◇) MH6; (▼) MH14.

Figure 3A:
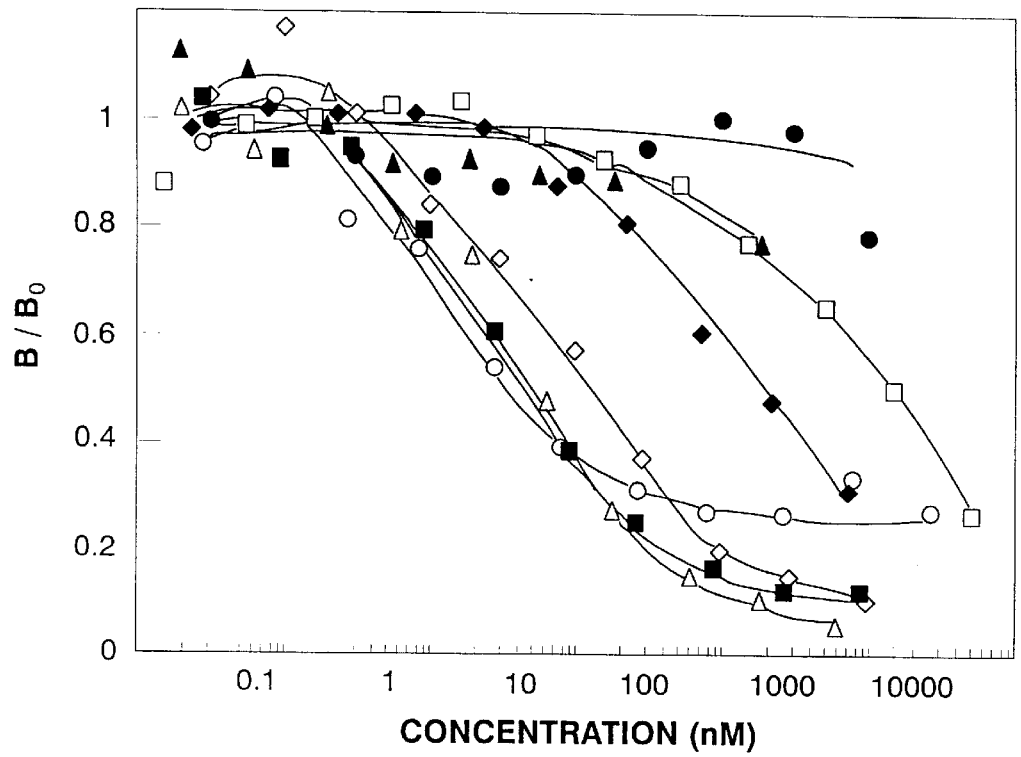

FIG. 3(A) Competitive inhibition of [$^{125}$I]hLIF binding to COS cells transfected with the hLIF-R α-chain by mLIF, hLIF and a selection of m-hLIF hybrids, (●) mLIF; (○) hLIF; (▲) MH1; (△) MH2; (□) MH4; (◆) MH5; (◇) MH6; (□) MH14. (B) Competitive inhibition by normal mouse serum of M1 colony differentiation induced by 200 U/ml mLIF, hLIF or m-hLIF hybrids, (●) mLIF; (○) hLIF; (△) MH2; (□) MH4; (◆) MH5; (◇) MH6.

FIG. 4 Comparison of mouse (SEQ. ID. NO:1), human (SEQ. ID. NO:2) and porcine (SEQ.ID.NO:3) LIF and G-CSF (SEQ ID NO:4) amino acid sequences. Amino acid residues that are identical between mLIF and hLIF are indicated by asterisks and predicted α-helices A, B, C and D in hLIF are marked within boxes. Numbering of the amino acid residues of each protein is indicated as starting at the first serine of the mature protein. The first glycine is −1 and is derived by thrombin cleavage of GST-LIF fusion. The serine +1 is equivalent to serine +24 of the immature native protein.

The figure also shows the alignment of LIF proteins to hG-CSF and the secondary structure assignments for G-CSF. (H, α-helix; G, 3$_{10}$-helix turn; T, turn; S, bend).

Figure 5A:
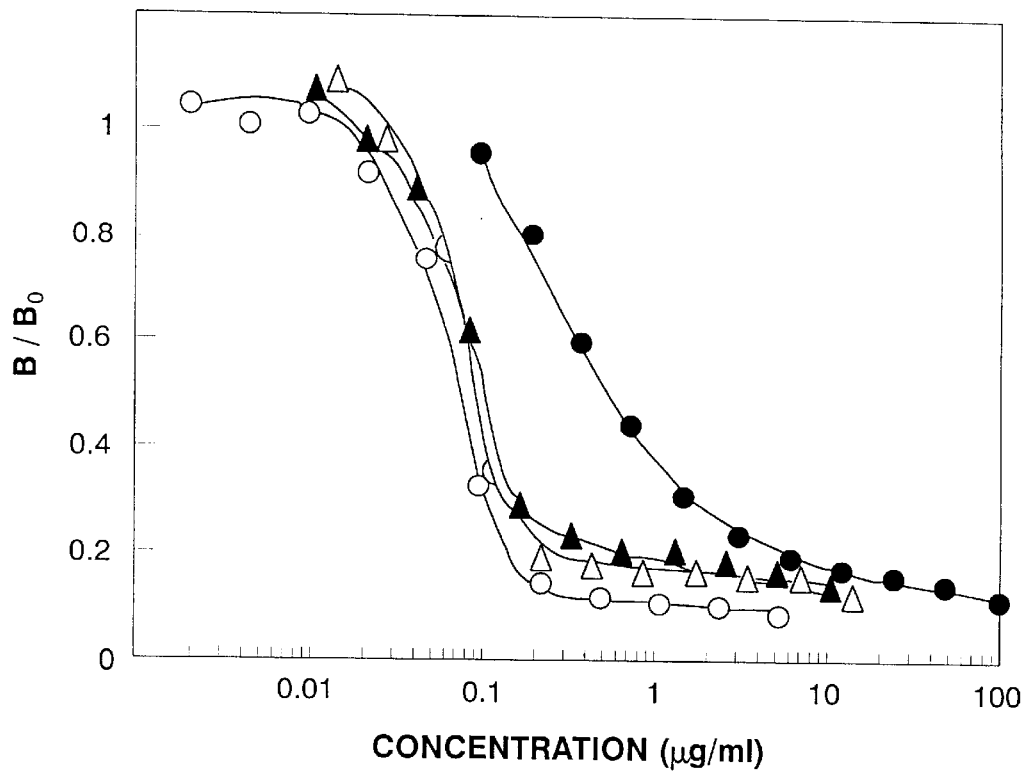
Figure 5B:
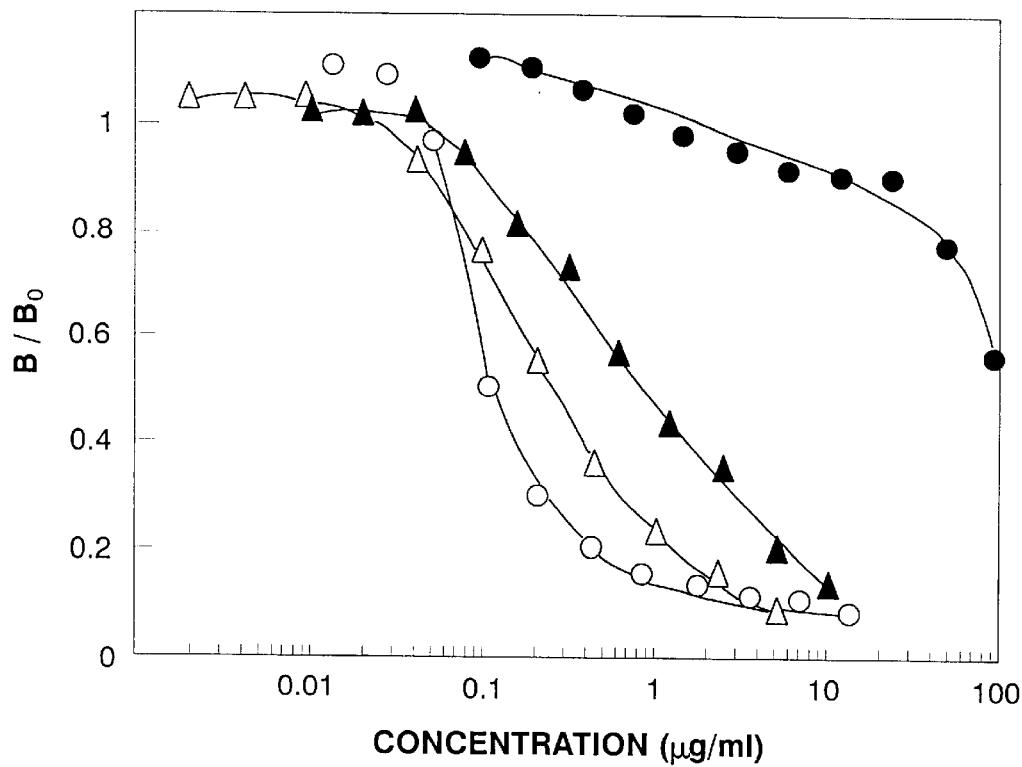
Figure 5C:
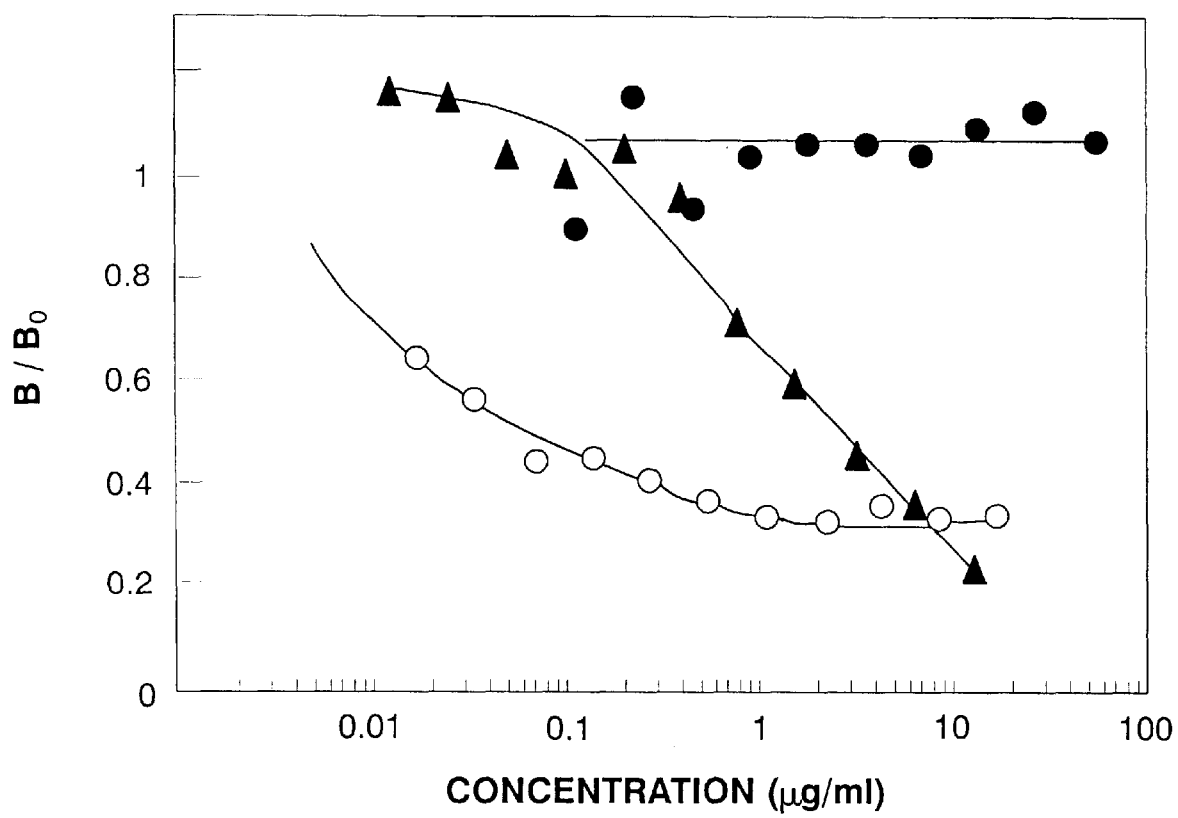

FIG. 5 is a graphical representation showing:
(A) competitive inhibition of $^{125}$I-mLIF binding to mLBP (soluble mLIF-R α-chain) by mLIF (●), hLIF (○), MH33 (▲) and MH2 (△);
(B) competitive inhibition of $^{125}$I-hLIF binding to mLBP by mLIF (●), hLIF (○), MH33 (▲) and MH2 (△); and
(C) competitive inhibition of $^{125}$I-hLIF binding to COS cells transfected with the hLIF-R α-chain by mLIF (●), hLIF (○) and MH33 (▲);
results for all competition assays are expressed as the number of counts bound to the receptor at a particular concentration of unlabelled inhibitor (B) over the number of counts bound to the receptor when no unlabelled inhibitor is present (B$_0$).

Figure 6:
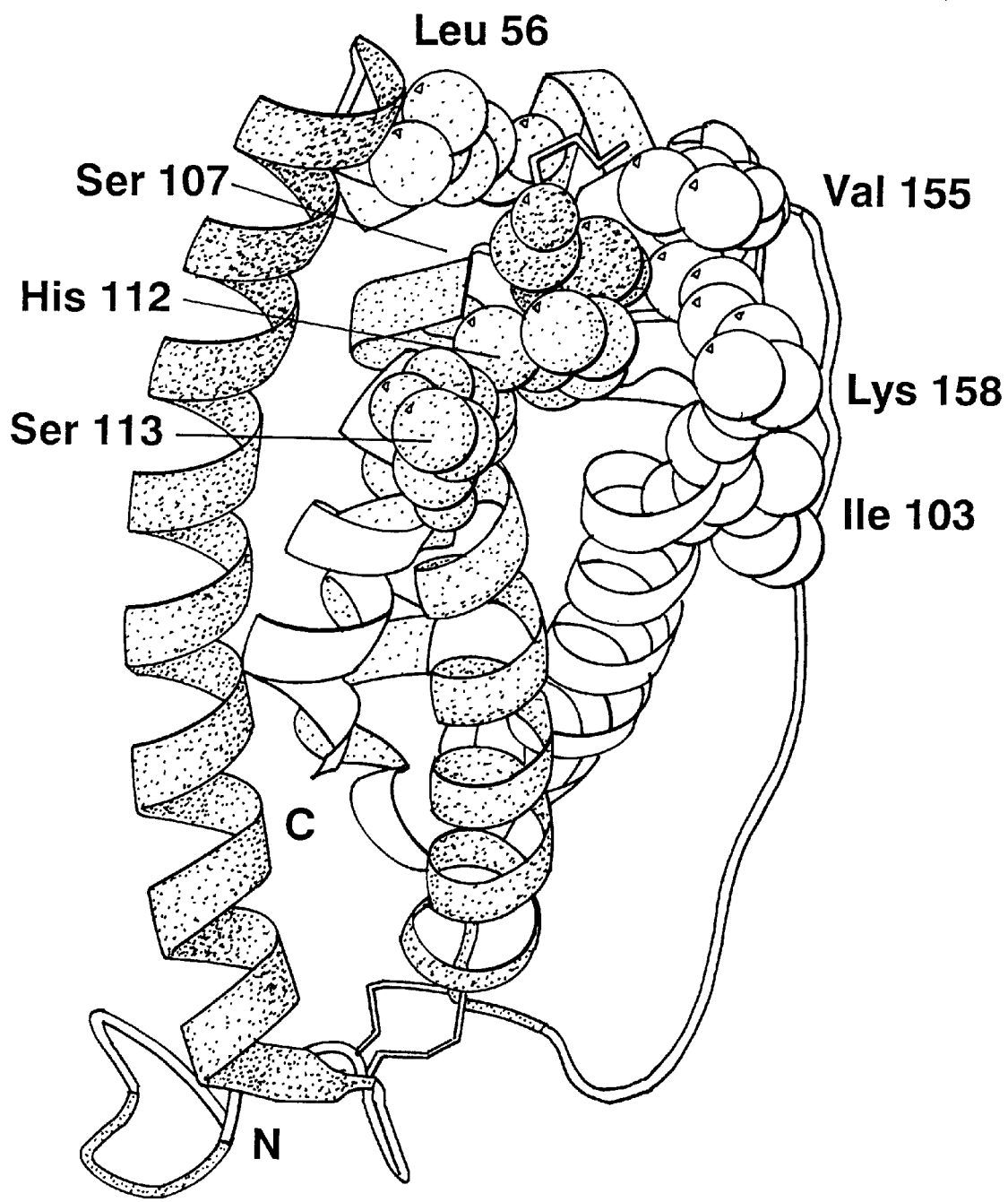

FIG. 6 is a pictorial representation showing a ribbon diagram of the model of hLIF with the receptor binding site amino acid residues shown in CPK form.

EXAMPLE 1

Construction of Hybrid LIF Proteins

Hybrid cDNAs in which portions of mouse LIF were replaced with homologous regions of human LIF (SEQ. ID. NO:2) were either synthesized from discrete restriction fragments of the two LIF cDNA molecules, or they were generated by the "splicing by overlap extension" method (Ho et al, 1989) which is a PCR-based technique using Pfu polymerase (Stratagene). The cDNA encoding porcine LIF (SEQ. ID. NO:3) was constructed from a genomic porcine LIF clone (Willson et al. 1992) in which the second intron was removed using the above PCR-based technique. The mutated cDNAs were subcloned into the E. coli expression vector pGEX-2T. All constructs were sequenced in both directions using T7 DNA polymerase (Pharmacia) and a Promega dideoxy sequencing kit.

Clones designated herein as MH1 and MH2 (Table 1 and FIG. 1) were constructed from plasmids pmLIF (in pGEX-2TH) and phLIF (in pGEX-2TH). Plasmid pmLIF was cut with the restriction enzymes SmaI and HindIII to produce fragments of approximately 257 bp and 5241 bp. Plasmid phLIF was also cut with the restriction enzymes SmaI and HindIII to produce fragments of approximately 258 bp and approximately 247 bp. The approximately 293 bp SmaI-HindIII mLIF fragment was ligated with the approximately 247 bp SmaI-HindIII hLIF fragment to give construct MH1. The approximately 258 bp SmaI-HindIII hLIF fragment was ligated with the approximately 240 bp SmaI-HindIII mLIF fragment to give construct MH2. LIF hybrid molecules are shown in Table 1 and FIG. 1.

EXAMPLE 2

Protein Expression

All cDNAs were expressed in E. coli NM522 except for MH 11(E. coli strain TOPP4, Stratagene). Growth and induction of transformants, lysis of cells, adsorption on glutathione agarose and thrombin cleavage of fusion proteins was carried out essentially as described (Smith and Johnson, 1988; Gearing et al. 1989) except that culture were induced by 50 μM IPTG in exponentially growing bacteria at 30° C. rather than 37° C. All mutants were further purified on a 10 cm×2 cm i.d. S-Sepharose column (Pharmacia, Uppsala) with a linear gradient of 0.2–0.45 M NaCl in 50 mM sodium phosphate pH7.0 over 45 minutes at a flow rate of 2.5 ml/min. The purity of each hybrid was confirmed by their elution as a single peak from a 100 mm×4.6 mm i.d. C8 RP-HPLC column (Brownlee) using a 0–100% v/v acetonitrile gradient in 0.1% v/v trifluoroacetic acid over 60 minutes at a flow rate of 1 ml/min and by electrophoresis on 15% w/v SDS-polycrylamide gels (Laemmli, 1970) in a Mini-Protean II system (Bio-Rad) followed by silver staining (Butcher and Tomkins, 1985). The concentration of protein in each preparation of purified hybrid was quantified by amino acid analysis on a Beckman amino acid analyser (model 6300) (Simpson et al, 1986) with norleucine added as an internal standard in all samples.

EXAMPLE 3

Radioiodination of Ligands

Recombinant mLIF or hLIF (1–2 μg) produced in E. coli was purified and iodinated as previously described (Hilton et al, 1988b). The iodinated materials retained biological activity and had specific activities of 3.5–4.5×10$^5$ c.p.m./pmol for [$^{125}$I]mLIF and 4–8×10$^5$ c.p.m./pmol for [$^{125}$I]hLIF.

EXAMPLE 4

Human LIF Receptor cDNA

A 4.1 kb cDNA encoding the human LIF receptor was isolated from a foetal liver cDNA library (Clonetech) by plaque hybridisation with a $^{32}$P-radiolabelled DNA fragment corresponding to amino acids 13–177. The nucleotide sequence corresponding to the coding region of this cDNA was determined by the dideoxynucleotide chain termination method (Sanger et al., 1977) using synthetic oligonucleotide primers. With the exception of a T to C nucleotide substitution at the third position of codon 555, which does not alter the predicted amino acid sequence, the sequence of this cDNA was otherwise identical to that previously reported (Gearing et al., 1991). The LIF-R cDNA was subcloned into the mammalian expression vector pCDM8 (Seed, 1987) and designated pCDM8/16C. The plasmid pCDM8/16CP, encoding a truncated soluble form of the hLIF-R that includes both haemopoietin domains and two of the three fibronectin repeat structures, was constructed from pCDM8/16C by deletion of a Pst1 fragment that codes for 97 membrane proximal residues, the transmembrane and cytoplasmic domains. The C-terminus of the soluble LIF-R encoded by pCDM8/16CP includes 10 residues encoded by vector sequences.

Transient expression of the hLIF-R in COS cells was achieved by electroporation with plasmid DNA. Briefly, $2 \times 10^7$ cells were harvested in 0.8 ml of phosphate-buffered saline (PBS), mixed with 20 µg of pCDM8/16C DNA at 4° C. and subjected to electroporation at 300 V and 500 µFD. Viable cells were harvested by centriftigation through a cushion of FCS and incubated in 50 ml of medium at 37° C. in an atmosphere of 10% v/v $CO_2$. Seventy-two hours post-transfection, cells were detached in HRF containing 0.04 M EDTA and 0.1 mg/ml chondroitin sulfate, harvested by centrifugation and resuspended in HRF.

EXAMPLE 5

Biological Activity of Mouse-Human Hybrid LIF Proteins

The functional activity of the m-hLIF hybrids was assayed by their ability to induce differentiation in murine M1 leukaemic colonies. M1 differentiation assays were performed as described (Metcalf et al, 1988). The specific activity of each hybrid was expressed as the units of M1 differentiation-inducing activity per milligram of protein.

For serum dose inhibition assays, the specific activity of each LIF preparation was determined by titration in cultures of M1 cells. Aliquots of normal mouse serum (containing approximately 5 µg/ml mLBP) were then added in serial 2-fold dilutions to cultures of M1 cells that also contained a just maximal concentration (200 U) of mLIF (SEQ. ID. NO:1), hLIF (SEQ. ID. NO:2) or m-hLIF hybrid. Assays including mLIF and hLIF gave identical results when either crude mouse serum or a highly purified preparation of mLBP was used. Hybrids were assessed for mLIF or hLIF character from the dilution of serum required to block 50% of their M1 cell differentiation-inducing activity.

EXAMPLE 6

Binding of Mouse-Human Hybrid LIF Proteins to Mouse LIF-Binding Protein (mLBP)

Normal mouse serum was used as a source of mLBP. For competitive binding experiments, 50 µl aliquots of unlabelled LIF or a mouse-human LIF hybrid were added to 96-well filtration assay plates containing a 0.65 micron Durapore membrane (Millipore, Mass., U.S.A.) with 20 µl aliquots of a 1/10 to 1/20 dilution of normal mouse serum, 10 µl radiolabelled ligand and 25 µl Concanavalin-A Sepharose 4B (ConA-Sepharose, Pharmacia, Uppsala) (diluted 1:4 in 100 mM sodium acetate pH6.0 containing 1 mM $MnCl_2$, 1 mM $MgCl_2$ and 1 mM $CaCl_2$; this and all subsequent buffers contained 0.02% w/v sodium azide and 0.02% v/v Tween 20) and incubated at room temperature overnight with agitation. Bound and free radioactivity were separated by vacuum filtration of the supernatant and the ConA-Sepharose pellet was washed once with 200 µl cold PBS. Assay plates containing the cell pellet were then exposed to a phosphor screen (Molecular Dynamics, Calif., U.S.A.) for 16–24 hours and the results quantified using Imagequant version 3.0 software (Molecular Dynamics).

EXAMPLE 7

Binding of the Mouse-Human LIF Hybrids to COS Cells Transfected With a hLIF-R cDNA Clone A cDNA encoding the hLIF-R was isolated, subcloned and expressed in COS cells as described in the above examples.

For competitive binding experiments, 20 µl aliquots of cells, resuspended in HRF at $5 \times 10^6 - 8 \times 10^6$ cells/ml, were added to 96 well filtration assay plates containing a 0.65 micron Durapore membrane (Millipore, Mass., U.S.A.) with 50 µl unlabelled LIF or m-hLIF hybrid and 10 µl $^{125}$I-hLIF and incubated overnight on ice. Bound and free radioactivity were separated by vacuum filtration of the supernatant and the cell pellet was washed once with 200 µl cold PBS. Assay plates containing the cell pellet were then exposed to a phosphor screen (Molecular Dynamics, Calif., U.S.A.) for 2–3 days and the results quantified using Imagequant version 3.0 software (Molecular Dynamics).

EXAMPLE 8

Mapping of Receptor-Binding Determinant on LIF

1. Hybrids MH1 to MH17

Secondary and tertiary structural predictions have suggested that the LIF molecule is an anti-parallel, four α-helical bundle, a topology common to a number of growth factors and cytokines (Diedrichs et al, 1991; Parry et al, 1991; de Vos et al, 1992). The model of Bazan (1991) was used to divide the LIF amino acid sequence into a series of modules of predicted α-helices and connecting loops. A series of plasmids was then designed to encode mouse-human chimeric LIF (m-hLIF) molecules (FIG. 1) in which regions of hLIF sequence were incorporated into a mLIF molecular framework. As the sequences of mLIF (SEQ. ID. NO:1) and hLIF (SEQ. ID. NO:2) are ~80% identical (Gough et al, 1988) (FIG. 4), swapping even large domains of mLIF and hLIF sequence resulted in changes of relatively few amino acid residues.

The protein concentration of each purified sample was determined by amino acid analysis, and the amount of biologically active protein in each sample was estimated by its ability to induce differentiation in mouse M1 myeloid leukaemic colonies. An internal standard of mLIF ($10^4$ U/ml) was used to normalise all M1 cell bioassays (50 U/ml of LIF is defined as the concentration of LIF required for half maximal stimulation). The specific biological activity of each hybrid on mouse cells was defined by the number of units of LIF activity per milligram of protein and was found to be within the normal range for both mLIF and hLIF ($1-3 \times 10^8$ U/mg) (FIG. 1) indicating that joining structural elements of these homologous proteins did not significantly disrupt their tertiary structure, nor affect their activity on mouse cells.

The structural integrity of all m-hLIF chimeras was also verified by evaluating their ability to bind correctly to the mLIF-R α-chain. Mouse LIF (SEQ. ID. NO:1), hLIF (SEQ. ID. NO:2) and all hybrids had a similar ability to compete for [$^{125}$I]mLIF binding to mLBP (FIG. 2A).

The first feature of hLIF (SEQ. ID. NO:2) that distinguishes it from mLIF (SEQ. ID. NO:1), i.e. its ability to bind to the hLIF-R α-chain, was evaluated by the ability of each hybrid to compete with [$^{125}$I]hLIF for binding to COS cells expressing the hLIF-R α-chain (COS hLIF-R cells). The second feature of hLIF that distinguishes it from mLIF, i.e. its ability to bind to the mLIF-R with a higher affinity than mLIF, was evaluated by the ability of each hybrid to compete with [$^{125}$I]hLIF for binding to mLBP and by its sensitivity to biological inhibition by mLBP.

The 1000- to 5000-fold difference in the ability of mLIF and hLIF to compete with [$^{125}$I]hLIF for binding to mLBP provided a large window in which to measure the degree of hLIF-like specific binding of each chimeric protein. In each assay, the doses of hLIF, mLIF and m-hLIF hybrid required to inhibit 50% of [$^{125}$I]hLIF binding to mLBP ($ID_{50}$) were measured, and hLIF and mLIF were defined as having 100% and 0% hLIF-like binding activity, respectively. Assays could then be normalised for inter-assay variations by using a logarithmic scale to convert the $ID_{50}$ for hLIF and mLIF to a score of 100% and 0%, respectively, then converting the $ID_{50}$ for each hybrid to a percentage score between these two extremes.

Figure 2B:
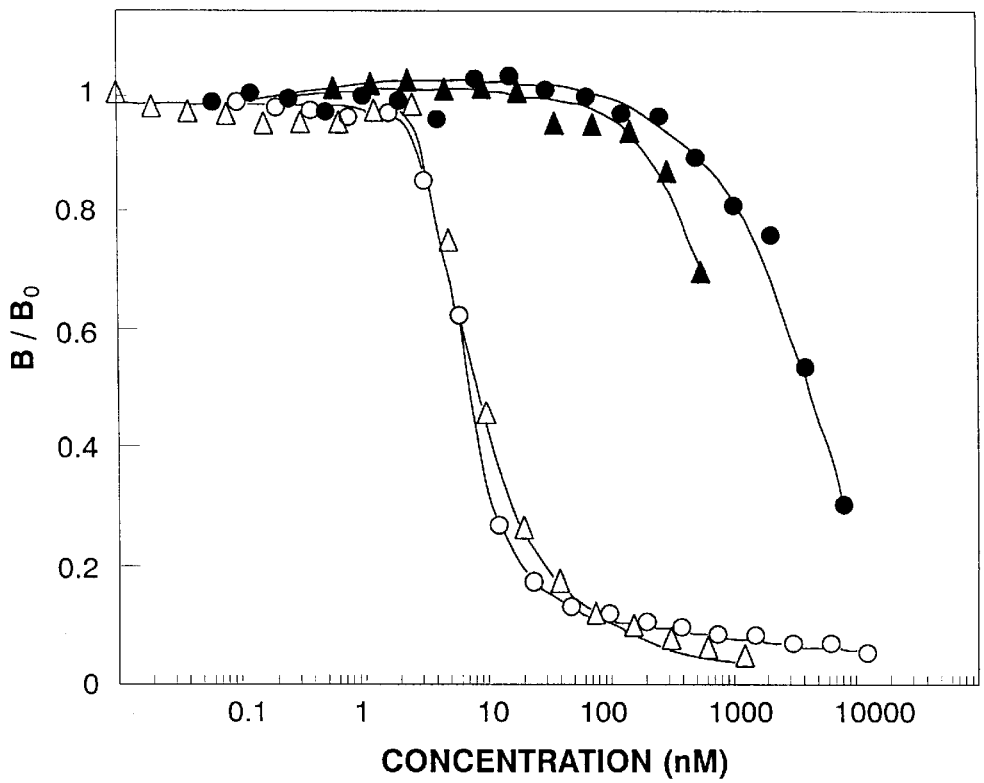

Initial experiments found that a hybrid LIF molecule (MH2), in which the amino-terminal half contained mLIF amino acid residues and the carboxy-terminal half consisted of hLIF residues, had 87±4% (mean±SEM) hLIF-like activity for binding to mLBP, and had gained the capacity to bind to the hLIF-R α-chain. In contrast, the reverse hybrid (MH1) had only ~23±3% hLIF-like binding to mLBP (FIG. 2B) and could not bind to COS hLIF-R cells. These results defined the carboxy-terminal half of hLIF as containing a major receptor binding determinant.

Figure 2C:
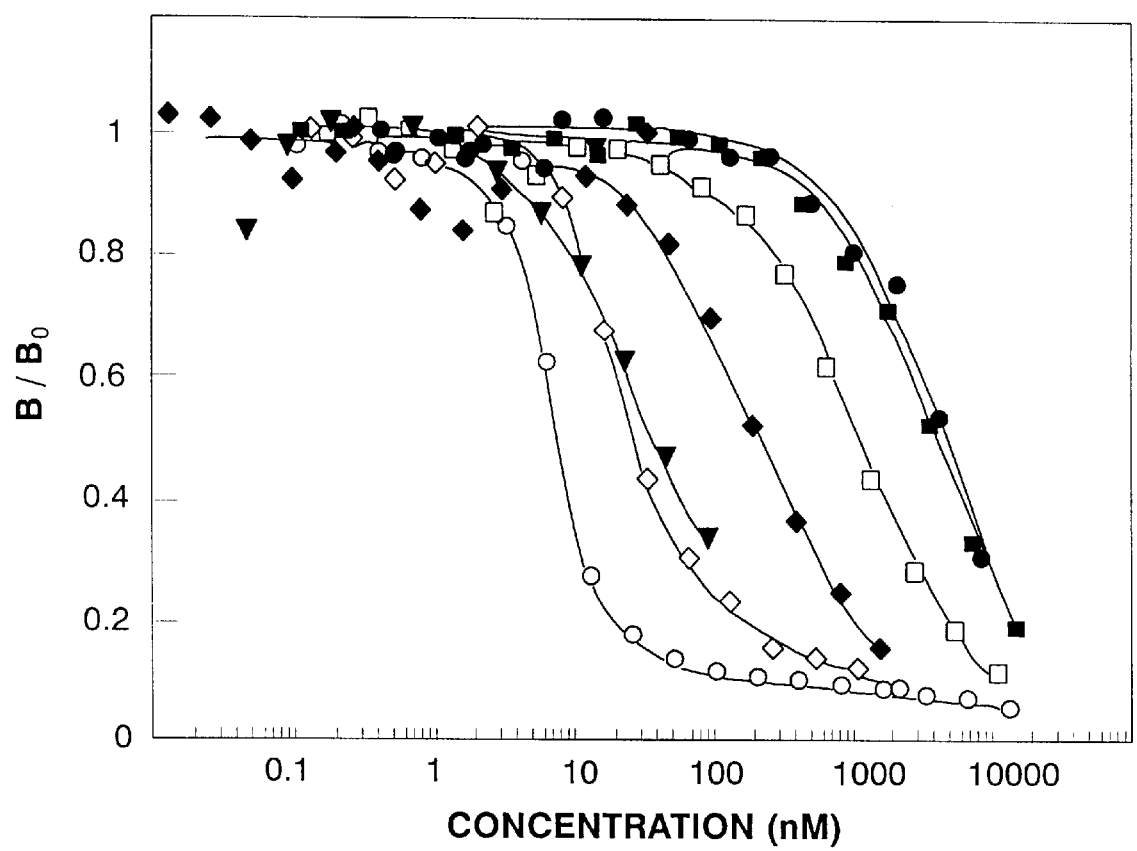

Hybrids MH3, MH4, MH5 and MH6 were constructed to resolve which structural modules were involved in the receptor binding site. When the predicted D-helix was composed of hLIF residues (MH3), the hybrid had no hLIF-like binding to mLBP. When the predicted C-helix was composed of hLIF residues (MH4), the hybrid displayed 26±1% hLIF-like activity in its ability to compete for [$^{125}$I]hLIF binding to mLBP (FIG. 2C). Hybrid MH5, which contained the predicted C-D loop region substituted for the equivalent hLIF residues, displayed 52±1% hLIF-like activity in the same assay. The combination of hLIF residues in both the predicted C-helix and the C-D loop (MH6) resulted in a hybrid with 78±2% hLIF-like activity as assessed by its ability to compete for [$^{125}$I]hLIF binding to mLBP (FIG. 2C). Hybrids MH7, MH8 and MH9 were constructed in order to test whether the D-helix co-operated with either the C-helix or the C-D loop to enhance hLIF-like binding specificity. Hybrid MH7, which contained hLIF sequences in the C-D loop and in the D-helix, behaved like hybrid MH5, which contained hLIF residues in the C-D loop only. Hybrid MH9, which contained hLIF residues in the C-helix and the D-helix, behaved like hybrid MH4, in which only the C-helix comprised hLIF sequence. Hybrid MH8, which contained hLIF residues in the C-helix, C-D loop and D-helix, behaved like hybrid MH6, in which only the C-helix and C-D loop comprised hLIF sequence (FIG. 1).

All chimeras were also tested for their ability to compete with [$^{125}$I]hLIF for binding to COS hLIF-R cells. A typical example of a competitive binding assay between the chimeras and [$^{125}$I]hLIF on COS hLIF-R cells is shown in FIG. 3A. When the hybrids were ranked according to the dose required to produce 50% inhibition ($ID_{50}$) of [$^{125}$I]hLIF binding to either mLBP or COS hLIF-R cells, the hierarchy was the same in each assay (FIG. 1) indicating that the two features of hLIF that distinguish it from mLIF (SEQ. ID. NO:1) map to the same regions on the hLIF (SEQ. ID. NO:2) molecule.

Single amino acid substitutions were then used to identify the individual amino acids within the C-helix that were critical for hLIF-like binding to both mLBP and COS hLIF-R cells. Hybrid MH8, which had 77±3% hLIF-like binding to mLBP, was used as a framework for these constructs. The residues most likely to contribute to hLIF-specific binding in the C-helix are those that are different in mLIF and hLIF, and are predicted on the basis of a helical wheel projection to be on the external (hydrophilic) surface of the molecule. There were therefore three amino acids in the C-helix of hLIF (H112, S113, and I121) that were candidates for investigation by site-directed mutagenesis, although residue I121 represented a conservative substitution between mLIF (A) and hLIF (I) and so was discounted. Residues H112 and S113 were mutated individually to their equivalent mLIF residue in hybrids MH11 and MH12, respectively. If either residue was important for hLIF-like binding, its substitution to the equivalent mLIF residue should reduce the hLIF-like binding of the hybrid, perhaps to a level similar to that of hybrid MH5, in which only the C-D loop contains hLIF residues. The hLIF-like binding of hybrids MH11 and MH12 to mLBP was scored as 67±1% and 73±3%, respectively, indicating that the substitution H112Q was the more significant of these mutations, but alone was insufficient to abrogate completely the contribution of the C-helix to hLIF-like binding to mLBP. Hybrid MH 10, which comprised an MH8 framework with a residue in the D-helix, K168, swapped to its mLIF equivalent (T168), showed that changing the least conserved residue on the external face of the D-helix did not affect hLIF-like binding.

In order to test whether hLIF-like binding activity of hybrid MH5, in which the C-D loop contains hLIF sequence, could be restored to the level of hybrid MH6, in which both the C-D loop and the C-helix consist of hLIF residues, mLIF amino acids Q112, V113 in the C-helix and T168 in the D-helix were substituted with their equivalent hLIF residues. Hybrid MH14, which was based on hybrid MH5 but with additional substitutions Q112H and V113S, showed 71±2% hLIF-like binding to mLBP, indicating that these two residues define the contribution of the C-helix to hLIF-specific binding (FIG. 2C). Hybrid MH113, which was identical to hybrid MH14 except for an additional T168K mutation, also had 73±3% hLIF-specific binding to mLBP, confirming that the mutated residues in the C-helix were sufficient to restore MH6-like mLBP binding. These chimeras were also tested for their ability to compete with [$^{125}$I] hLIF binding to both mLBP and COS hLIF-R cells and gave qualitatively the same results in both assays (FIG. 1). This strategy has, therefore, identified two residues within the C-helix, H112, and S113, as critical for hLIF-like binding to both mLBP and the hLIF receptor.

Figure 3B:
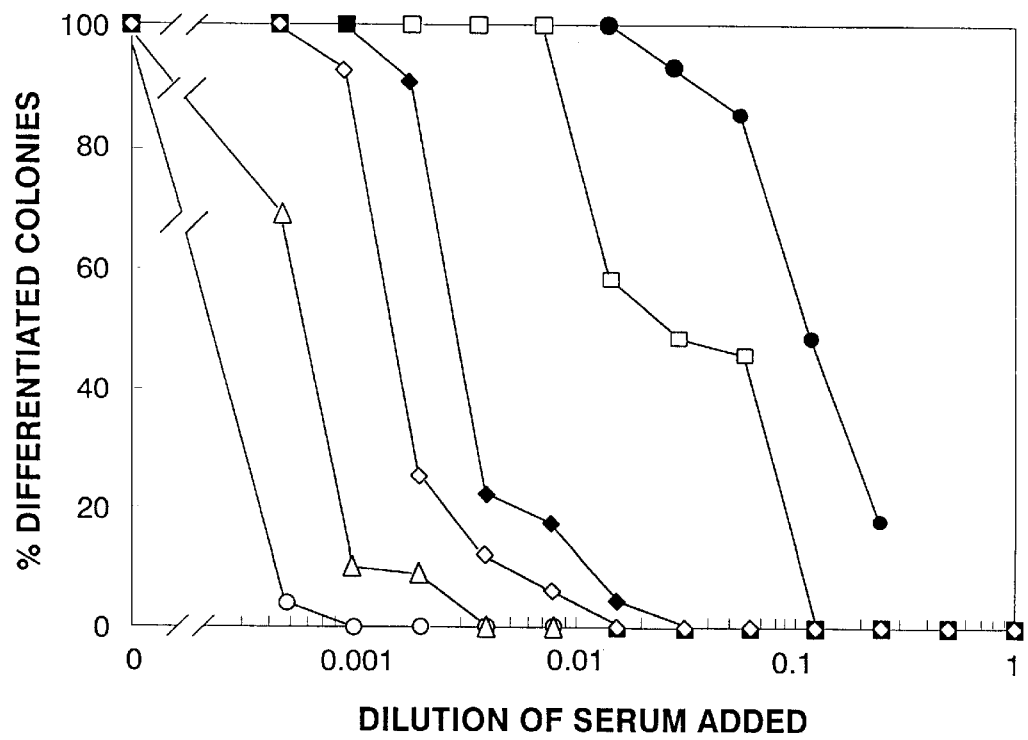

A 1:4 to 1:8 dilution of normal mouse serum (equivalent to ~0.5–1 μg/ml mLBP) is required to block 50% of the M1 differentiation-inducing activity of up to 200 U/ml mLIF, whereas, due to the higher affinity of hLIF for mLBP, a 1:8192 dilution of serum (~0.6 ng/ml mLBP) is sufficient to block 50% of the M1 activity of up to 200 U/ml hLIF. This ability of mLBP to inhibit the differentiation-inducing activity of LIF in a species-specific manner was utilized as a second assay that distinguished hLIF from mLIF. Hybrids were also assessed for hLIF-like activity in this assay according to the dose of serum required to inhibit 50% of their M1 cell differentiation-inducing activity when they were present in the culture dish at a just maximal stimulatory concentration (~200 U/ml). An example of a typical serum dilution M1 assay is shown in FIG. 3B. All data from this assay were consistent with the data obtained from the competitive binding assays with mLBP and [$^{125}$I]hLIF (FIGS. 2B and 2C), thus eliminating the possibility that the higher affinity of hLIF for mLBP was an artefact of the binding assays themselves or of the use of iodinated hLIF.

A strategy similar to that used to define the important residues for hLIF binding to the hLIF-R in the predicted C-helix has been used for identifying single amino acid residues in the C-D loop region that are critical for hLIF-like activity. Hybrids in which the C-D loop had been subdivided were constructed. Hybrids MH16 and MH17 are based on a MH4 framework, with MH16 having the first half of the C-D loop (residues 131–153) substituted for hLIF residues and MH17 having the second half of the C-D loop (residues 154–160) swapped (see Table 1).

When the predicted C-helix plus residues 131–153 of the C-D loop consisted of hLIF residues (MH16), the hybrid had a greater hLIF-like character than MH4 (50% vs. 23%), indicating that there was a small contribution to hLIF-like binding to the hLIF-R α-chain by residues 131–153. When the C-helix plus residues 154–160 of the C-D loop consisted of hLIF residues (MH17), the hybrid displayed 94% hLIF-like activity in its ability to compete for $^{125}$I-hLIF binding to mLBP. This result defined D154–K166 as the major binding determinant within the C-D loop.

2. Hybrids MH18–MH41

The strategy for mutagenesis was to divide the LIF molecule into predicted secondary structural units of α-helix and connecting loop, test the contribution of each structural unit to hLIF-specific binding, then to ascertain the individual amino acids in that region that were responsible for that contribution.

Residues in the C-D loop were initially investigated. The assays used were found to be best able to discriminate between hybrids in the middle of their range, so hybrid MH6 which had 78±2% hLIF-like activity, was chosen as a basis for hybrids MH18–25 and MH31. Amino acid residues in the C-D loop that were different between mLIF and hLIF were individually swapped from the hLIF residue to the equivalent mLIF residue, and the resulting chimeras tested for a decrease in hLIF-like activity relative to MH6. Hybrids MH24 and MH25 showed a significant decrease in their % human score and their affinity for the hLIF-R α-chain relative to hLIF, and thus defined residues Val 155 and Lys 158 as being the two residues in the C-D loop that were responsible for its contribution to the overall hLIF-like activity.

The residues in the B-C loop region were then investigated, as previous comparisons of hybrids MH6 and MH8 versus MH2 and MH 15 (Example 8(i)) indicated that the region between Ile 103 and Leu 109, which is predicted to form the B-C loop as well as the last two residues of the B-helix, contributed to hLIF-specific binding. Hybrid MH5 (52± 1% hLIF-like activity) was chosen as a basis for hybrids MH29, MH30 and MH32. Amino acid residues in the region between residues 103–109 that were different between mLIF (SEQ. ID. NO:1) and hLIF (SEQ. ID. NO:2) were individually swapped from the mLIF residue to the equivalent hLIF residue, and the resulting chimeras tested for an increase in hLIF-like activity relative to MH5. Hybrid MH29 showed an increase in hLIF-like activity in terms of binding to both the mLIF-R α-chain and the hLIF-R α-chain, as did hybrid MH32 to a lesser extent, thus defining residues Ser 107 as being the residue in the region between residues 103–109 that was responsible for its contribution to the overall hLIF-like activity.

Assuming that the contribution of each amino acid to hLIF-specific activity was additive, hybrid MH33 was constructed in order to test that the residues identified in the C-helix, the C-D loop and the B-C loop could be substituted onto a mLIF framework, and reconstitute hLIF-like activity. Hybrid MH33 was a mouse framework molecule that contained the human LIF residues His 112 and Ser 113 from the C-helix, Val 155 and Lys 158 from the C-D loop, and had 72±3% hLIF-like activity (FIG. 5B) and had only an 8-fold lower affinity for the hLIF-R α-chain compared to hLIF (FIG. 5C), indicating that only 5 residues out of 180 conferred approximately three-quarters of the binding energy of hLIF.

The additional 25% of the binding energy of hLIF must reside in the N-terminal half of the molecule, so hybrids MH34–36 were based on MH33, but either the N-terminal tail and the A-helix, the A-B loop or the B-helix were swapped from mLIF sequence to hLIF sequence. There was no contribution to hLIF-specific activity from the N-terminal tail, the A-helix or the B-helix, but there was a large contribution from the A-B loop (FIG. 1). The contribution was subsequently shown to be in Asp 57.

EXAMPLE 9

LIF was aligned to G-CSF (SEQ. ID. NO:4) using the known hLIF (SEQ. ID. NO:2) and hG-CSF amino acid sequences and the multiple sequence alignment software of Smith (1986). The alignment is shown in FIG. 4. Modelling was performed using the Homology module of the Insight software system (Biosoft Inc, San Diego) and refined using the X-PLOR package (Brunger, 1992). LIF is most closely related to OSM, CNTF, G-CSF and IL-6 (Bazan, 1991), however, G-CSF (SEQ. ID. NO:4) was used as a basis for the model as it is the only known structure of this group. The helices of the 4 α-helical bundle were designated A, B, C and D (ordered from the N-terminus) and the loops were labelled according to the helices they join. The helical segments in G-CSF (SEQ. ID. NO:4) were treated as structurally conserved regions and their co-ordinates copied to the LIF model. The region Cys 131-Ser 135 was deemed not to be part of the C-helix so as not to constrain the disulfide bridges. Both G-CSF and GH (de Vos et al, 1992) have a $3_{10}$-helix in the A-B loop, close to the A-helix, so this structural motif was also conserved and copied to the model, while the remainder of the A-B loop was copied from a loop search of the protein data bank (Bernstein, 1977). The B-C loop and C-D loop from hG-CSF were used as models for the equivalent loops in hLIF. The N-terminal loop was built by the homology module of Insight.

Refinement of the model was performed in several stages. The disulfide bond pairs (Nicola et al, 1993) were defined, then the model was energy minimised with the Cα co-ordinates of all regions except for the N-terminal loop held fixed, to allow the segment joins and disulfide bridges to form. The model was then surrounded by 4 layers of water. The initial refinement used simulated-annealing starting at 600° K, then reducing by 300° K in steps of 50° K over 0.5 or 1.0 pico-seconds, followed by 5 pico-seconds of molecular dynamics at 300° K. To assist in maintaining a helical structure, the side chains and loops were allowed to relax with an i-i+4 O-H distance constraint of 2.2 Å on the helices of the 4 α-helical bundle. This was then followed by 10 pico-seconds of unrestrained molecular dynamics. The resulting model is shown in FIG. 6 as a ribbon diagram (Kraulis, 1991) with the receptor binding site amino acids shown in CPK form.

Since mLIF (SEQ. ID. NO:1), hLIF (SEQ. ID. NO:2) and all m-hLIF chimeras had an approximately equal ability to compete with [$^{125}$I]mLIF binding to the soluble mLIF-R α-chain, and had nearly equal biological activities in a mouse cell bioassay they must contain a common binding site for the α-chain of the mLIF-R. This binding site on the ligand (site a) presumably comprises conserved amino acid residues in the mLIF and hLIF proteins and so is invisible in our assay system. This site, however, is not sufficient to mediate binding to the hLIF-R α-chain, or to generate enhanced binding to the mLIF-R α-chain, which are exclusive properties of hLIF. A second site on the hLIF molecule, which we have mapped in these studies (site b) is comprised of a small number of residues in the predicted C-D loop, C-helix and B-C loop of hLIF and is proposed to mediate the exclusive properties of hLIF (SEQ. ID. NO:2). These residues form a cluster on one face of the predicted three-dimensional structure of hLIF (FIG. 6).

The primary interaction site on the LIF ligand for its isologous receptor α-chain is not the same in the human and mouse systems. It is proposed that hLIF (SEQ. ID. NO:2) but not mLIF (SEQ. ID. NO:1) is able to recognise a site which is conserved in both the hLIF and mLIF receptor α-chains (site B), while the primary binding site for mLIF on the mLIF-R α-chain (site A), is not present on the hLIF-R α-chain. This proposed model potentially explains the low-affinity binding of mLIF and hLIF to their isologous receptor α-chains, the inability of mLIF to bind to the hLIF-R α-chain, and the apparent identity of the sites on the hLIF molecule that mediate both the high-affinity binding to the mLIF-R α-chain and binding to the hLIF-R α-chain. This appears to be the simplest model consistent with these data.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Table Legends

Table 1

Amino acid sequence specifications for m-hLIF chimeric proteins. Sequences are designated according to the following example. M1–130: H131–160: M161–180 (MH5) denotes that residues between 1 and 130 as well as between 161 and 180 are derived from mLIF sequence (SEQ. ID. NO:1) and residues 131–160 are derived from hLIF sequence. Single amino substitutions are denoted as H138R, indicating that the histidine at position 138 is changed to arginine.

TABLE 1

| HYBRID | AMINO ACID SEQUENCE SPECIFICATION |
|---|---|
| M | M1–180 |
| H | H1–180 |
| MH1 | H1–102:M103–180 |
| MH26 | H1–109:M110–180 |
| MH2 | M1–102:H103–180 |
| MH3 | M1–160:H161–180 |
| MH4 | M1–109:H110–130:M131–180 |
| MH5 | M1–130:H131–160:M161–180 |
| MH6 | M1–109:H110–160:M161–180 |
| MH15 | M1–102:H103–160:M161–180 |
| MH7 | M1–130:H131–180 |
| MH8 | M1–109:H110–180 |
| MH9 | M1–109:H110–130:M131–160:H161–180 |
| MH10 | MH8 + K168T |
| MH11 | MH8 + H112Q |
| MH12 | MH8 + S113V |
| MH13 | MH5 + Q112H:V113S:T168K |
| MH27 | MH5 + Q112H |
| MH28 | MH5 + V113S |
| MH14 | MH5 + Q112H:V113S |
| MH16 | M1–109:H110–153:M154–180 |
| MH17 | M1–109:H110–130:M131–153:H154–160:M161–180 |
| MH18 | MH6 + H138R |
| MH31 | MH6 + T145P |
| MH19 | MH6 + Y146P |
| MH20 | MH6 + G147V |
| MH21 | MH6 + T150H |
| MH22 | MH6 + G152D |
| MH23 | MH6 + D154E |
| MH24 | MH6 + V155A |
| MH25 | MH6 + K158R |
| MH29 | MH5 + T107S |
| MH30 | MH5 + V109L |
| MH32 | MH5 + V103I |
| MH33 | M + T107S:Q112H:V113S:A155V:R158K |
| MH34 | MH33 + H1–47 |
| MH35 | MH33 + H48–81 |
| MH36 | MH33 + H82–104 |
| MH37 | MH33 + V103I |
| MH38 | MH33 + V56L |
| MH39 | MH33 + V109L |
| MH40 | MH33 + V56L:V103I:V109L |
| MH41 | MH33 + V56L:V103I |

REFERENCES

Abdel-Meguid, S S et al., *Proc Natl Acad Sci USA* 84: 6434–7 (1987).
Bazan, J F *Proc Natl Acad Sci USA* 87: 693–8 (1990).
Bazan, J F *Immunol Today* 11: 350–4 (1990).
Bazan J F *Neuron* 7(2): 197–208 (1991).
Bernstein, *J. Mol. Biol.* 122: 535–542 (1977).
Blundell T et al *Eur. J. Biochem.* 172; 513–520 (1988).
Brandhuber, B J, T. Boone, W. C. Kenney, D. B. McKay, *J Biol Chem* 262:12306-(1987).
Brunger, A T "X-PLOR, a system for crystallography and NMR." Yale Univ., New Haven, Conn. (1992).
Butcher L A and J K Tomkins *Anal. Bioch* 148:384–388 (1985).
Cosman, D et al., *Trends Biochem Sci* 15: 265–70 (1990).
Diederichs, K, T. Boone, P. A. Karplus, *Science* 254: 1779–82 (1991).
Gearing D P, Nicola N A, Metcalf D, Foote S, Willson T A, Gough N M and Williams L *BioTechnology* 7: 1157–61 (1989).
Gearing D P, et al., *EMBO J* 10:2839–48 (1991).
Gearing D P, et al., *Science* 255: 1434–7 (1992).
Gough N M, et al., *Proc. Natl. Acad. Sci. USA* 85: 2623–2727, (1988).
Hill C P, T. D. Osslund, D. Eisenberg, *Proc Natl Acad Sci USA* 90: 5167–71 (1993).

Hilton D J, Nicola N A and Metcalf D *Anal. Biochem.* 173(2): 359–67 (1988a).

Hilton D J, Nicola N A and Metcalf D *Proc. Natl. Acad. Sci. USA* 85(16): 5971–5 (1988b).

Ho S N, Hunt H D, Horton R M, Pullen J K and Pease L R, *Gene* 77(1): 51–9 (1989).

Kraulis P J, *J. Appl. Cryst.* 24: 946–950 (1991).

Layton M J, Cross B A, Metcalf D, Ward L D, Simpson R D and Nicola N A *Proc. Natl. Acad. Sci. USA* 89: 8616–20 (1992).

Metcalf D *Int. J. Cell Cloning* 9(2): 92–108 (1991).

Metcalf D et al., *Leukaemia* 2: 216–221, (1988).

Milburn M V, et al., *Nature* 3 63: 172–6 (1993).

Nicola N A, B. Cross, R. J. Simpson, *Biochem. Biophys. Res. Comm.* 190: 20–6 (1993).

Owczarek C M, et al., *EMBO J* 12 3487–95 (1993).

Parry A D, et al., *J Mol. Recog.* 4: 63–75, (1991).

Powers R, et al., *Science* 256: 1673–7 (1992).

Sanger F A, Nicklen S and Coulson A R *Proc. Natl. Acad. Sci. USA* 74: 5463–7 (1977).

Seed B *Nature* 329: 840–842 (1987).

Smith D K, "Concepts and use of software for pair-wise and multiple genetic sequence alignment" Technical Report (School of Information Sciences and Engineering, 1986).

Smith D B and Johnson K S *Gene* 67(1): 31–40 (1988).

de Vos A M, M. Ultsch, A. A. Kossiakoff, *Science* 255: 306–12 (1992).

Willson T A, Metcalf D and Gough N M *Eur. J. Biochem.* 204(1): 21–30 (1992).

What is claimed is:

1. A substantially biologically pure molecule as set forth in FIG. 1 comprising:

(i) a polypeptide backbone having a tertiary structure;
   (ii) amino acid residues constituting a binding determinant for the a chain of hLIF binding receptor inserted into said polypeptide backbone such that the arrangement of said amino acid residues in the tertiary structure of the polypeptide provides a hLIF receptor-binding face;

and wherein said molecule exhibits at least about 50% hLIF-like activity as defined by the equation:

$$\frac{\log X_m - \log X_c}{\log X_m - \log X_h} \geq 0.50$$

wherein $X_m$ is a dose of unlabelled mLIF; $X_h$ is a dose of unlabelled hLIF; and $X_C$ is a dose of said molecule required to give 50% inhibition of $^{125}$I-hLIF binding to murine LIF binding protein.

2. The molecule according to claim 1 wherein the polypeptide backbone is a mammalian cytokine.

3. The molecule according to claim 2 wherein the cytokine is a non-human LIF.

4. The molecule according to claim 3 wherein the non-human LIF is from a livestock animal, laboratory test animal, companion animal or captive wild animal.

5. The molecule according to claim 4 wherein the non-human LIF is murine LIF.

6. The molecule according to claim 2 wherein the mammalian cytokine is a colony stimulating factor, an interleukin, oncostatin M, ciliary neurotrophic factor or a haemopoietic growth factor.

7. The molecule according to claim 6 wherein the mammalian cytokine is G-CSF (SEQ. ID. NO:4).

8. The molecule according to claim 1 wherein the amino acid residues constituting the hLIF receptor binding determinant are selected from at least one of the following predicted structural regions:
   (i) a region between the A and B helices;
   (ii) a region between the B and C helices;
   (iii) the C helix; and
   (iv) a region between the C and D helices.

9. A molecule according to claim 8 wherein the amino acid residues constituting the hLIF receptor binding determinant are Asp 57, Ser 107, His 112, Ser 113, Val 155 and Lys 158 of hLIF.

10. An isolated murine-human leukemia inhibitory factor (mhLIF) hybrid molecule, as set forth in FIG. 1 comprising a polypeptide backbone of murine LIF, wherein at least one amino acid of said murine LIF is substituted with an amino acid of human LIF thereby providing a binding determinant for the α-chain of a hLIF binding receptor, and wherein said hybrid molecule exhibits at least 50% hLIF-like activity as defined by the equation:

$$\frac{\text{LOG } X_m - \text{LOG } X_c}{\text{LOG } X_m - \text{LOG } X_h} \geq 0.50$$

wherein $X_m$ is a dose of unlabeled mLIF having SEQ ID NO:1; $X_h$ is a dose of unlabeled hLIF having SEQ ID NO:2; and $X_c$ is a dose of said molecule required to give 50% inhibition of $^{125}$I-hLIF binding to murine LIF binding protein.

11. The isolated mouse-human LIF hybrid molecule of claim 10, wherein the substitution on said mLIF comprises T107S, Q112H, V113S, A155V and R158K.

12. The isolated mouse-human LIF hybrid molecule of claim 11, further comprising an additional human LIF amino acid substitution on said mLIF at a region between the A and B helices set forth in SEQ ID NOS:1 and 2.

13. The isolated mouse-human LIF hybrid molecule of claim 12, wherein the amino acid at position 57 of mLIF is substituted with Asp.

14. The isolated mhLIF hybrid molecule of claim 10, wherein said hybrid molecule is selected from the group consisting of MH2, MH5, MH6, MH7, MH8, MH10, MH11, MH12, MH13, MH14, MH15, MH16, MH17, MH18, MH19, MH20, MH21, MH22, MH23, MH24, MH25, MH27, MH28, MH29, MH30, MH31, MH32, MH33, MH34, MH35, MH36, MH37, MH38, MH39, MH40 and MH41.

15. The isolated mouse-human LIF hybrid molecule of claim 14, wherein said molecule is selected from the group consisting of MH5, MH6, MH16, MH17, MH18, MH19, MH20, MH21, MH22, MH23, MH24, MH25, MH29, MH30, MH31, MH32, MH33, MH34, MH35, MH36, MH37, MH38, MH39, MH40 and MH41.

16. The isolated mouse-human LIF hybrid molecule of claim 15, wherein said molecule is MH33 or MH35.

17. An isolated nucleic acid molecule which encodes a substantially biologically pure molecule as set forth in FIG. 1 comprising:
   (ii) a polypeptide backbone having a tertiary structure;
   (ii) amino acid residues constituting a binding determinant for the α chain of hLIF binding receptor inserted into said polypeptide backbone such that the arrangement of said amino acid residues in the tertiary structure of the polypeptide provides a hLIF receptor-binding face;

and wherein said substantially biologically pure molecule exhibits at least about 50% hLIF-like activity as defined by the equation:

$$\frac{\log X_m - \log X_c}{\log X_m - \log X_h} \geq 0.50$$

wherein $X_m$ is a dose of unlabelled mLIF; $X_h$ is a dose of unlabelled hLIF; and $X_c$ is a dose of said substantially biologically pure molecule required to give 50% inhibition of $^{125}$I-hLIF binding to murine LIF binding protein.

18. An isolated nucleic acid molecule which encodes an isolated murine-human leukemia inhibitory factor (mhLIF) hybrid molecule as set forth in FIG. 1, comprising a polypeptide backbone of murine LIF, wherein at least one amino acid of said murine LIF is substituted with an amino acid of human LIF thereby providing a binding determinant for the α-chain of a hLIF binding receptor, and wherein said hybrid molecule exhibits at least 50% hLIF-like activity as defined by the equation:

$$\frac{\log X_m - \log X_c}{\log X_m - \log X_h} \geq 0.50$$

wherein $X_m$ is a dose of unlabeled mLIF having SEQ ID NO:1; $X_h$ is a dose of unlabeled hLIF having SEQ ID NO:2; and $X_c$ is a dose of said hybrid molecule required to give 50% inhibition of $^{125}$I-hLIF binding to murine LIF binding protein.

19. The nucleic acid molecule according to claim 17 or 18, wherein said nucleic acid molecule is cDNA.

20. An expression vector comprising the nucleic acid molecule according to claim 19.

21. A prokaryotic or eukaryotic cell comprising the nucleic acid molecule according to claim 17 or 18.

22. A prokaryotic or eukaryotic cell comprising the expression vector according to claim 20.

* * * * *